United States Patent
Alaparthi et al.

(10) Patent No.: US 10,494,450 B2
(45) Date of Patent: Dec. 3, 2019

(54) PROCESSES FOR PREPARATION OF SUGAMMADEX AND INTERMEDIATES THEREOF

(71) Applicant: Lakshmi Prasad Alaparthi, Vadodara (IN)

(72) Inventors: Lakshmi Prasad Alaparthi, Vadodara (IN); Palash Pal, Vadodara (IN); Sadasiva Rao Ginjupalli, Guntur (IN); Uday Sharma, Vadodara (IN); Talluri Bhushaiah Chowdary, Guntur (IN); Anand Vijaykumar Mantri, Vadodara (IN); Bharath Reddy Gade, Hyderabad (IN); Gaurav Kulkarni, Vadodara (IN)

(*) Notice: Subject to any disclaimer, the term of this patent is extended or adjusted under 35 U.S.C. 154(b) by 0 days.

(21) Appl. No.: 15/580,408

(22) PCT Filed: May 27, 2016

(86) PCT No.: PCT/IN2016/050159
§ 371 (c)(1),
(2) Date: Dec. 7, 2017

(87) PCT Pub. No.: WO2016/194001
PCT Pub. Date: Dec. 8, 2016

(65) Prior Publication Data
US 2018/0171033 A1    Jun. 21, 2018

(30) Foreign Application Priority Data

May 29, 2015    (IN) .................... 2089/MUM/2015
Mar. 14, 2016    (IN) .................... 201621008861

(51) Int. Cl.
     *C08B 37/16*      (2006.01)
     *A61K 31/724*      (2006.01)

(52) U.S. Cl.
     CPC ........ *C08B 37/0012* (2013.01); *A61K 31/724* (2013.01)

(58) Field of Classification Search
None
See application file for complete search history.

(56) References Cited

U.S. PATENT DOCUMENTS

2014/0221641 A1*    8/2014    Davuluri ............. C08B 37/0012
                                                               536/103
2018/0355070 A1*    12/2018    Cabri ........................ C08L 5/16

FOREIGN PATENT DOCUMENTS

WO    WO-2008052076 A2 *    5/2008    ............... C07H 1/00
WO    WO-2013056128 A1 *    4/2013    ............... C07H 5/02
WO    2014125501 A1    8/2014

OTHER PUBLICATIONS

Scifinder summary of reactions, downloaded from the internet Mar. 25, 2019.*
University of Calgary Synthesis of Sulfides, internet article, https://web.archive.org/web/20040129221943/http://www.chem.ucalgary.ca/courses/350/Carey5th/Ch16/ch16-7-1.html, published 2004.*

* cited by examiner

*Primary Examiner* — Layla D Berry
(74) *Attorney, Agent, or Firm* — Nadya Reingand; Yan Hankin

(57) ABSTRACT

The present invention relates to a process for preparation of 6-perdeoxy-6-per-chloro gamma-cyclodextrin which is a key intermediate useful in the synthesis of Sugammadex sodium. The present invention further relates to a process for preparation and purification of Sugammadex sodium.

8 Claims, 13 Drawing Sheets

PROCESSES FOR PREPARATION OF SUGAMMADEX AND INTERMEDIATES THEREOF

FIELD OF THE INVENTION

The present invention relates to process for preparation of 6-perdeoxy-6-per-chloro gamma cyclodextrin which is a key intermediate useful in the synthesis of Sugammadex sodium. The present invention also relates to a process for preparation of Sugammadex sodium from the said intermediate.

BACKGROUND OF THE INVENTION

Sugammadex (Org 25969, Bridion) is chemically known as Cyclooctakis-(1-→4)-[6-S-(2-carboxyethyl)-6-thio-α-D-glucopyranosyl]. Sugammadex is an agent for reversal of neuromuscular blockade by the neuromuscular blocking agents (NMBAs) rocuronium, vecuronium, pancuronium in general anesthesia. It is the first selective relaxant binding agent (SRBA). SRBAs are a new class of drugs that selectively encapsulates and binds NMBAs. The word Sugammadex is derived from Su=Sugar and Gamma cyclodex=Cyclodextrin. Sugammadex is inert chemically and does not bind to any receptor. It acts by rapidly encapsulating steroidal NMBDs to form a stable complex at a 1:1 ratio and thus decreasing the free concentration of the drug from the plasma. This creates a concentration gradient favoring the movement of the remaining rocuronium molecules from the neuromuscular junction back into the plasma, where they are encapsulated by free Sugammadex molecules. The latter molecules also enter the tissues and form a complex with rocuronium. Therefore, the neuromuscular blockade of rocuronium is terminated rapidly by the diffusion of rocuronium away from the neuromuscular junction back into the plasma.

NMBDs are quaternary ammonium compounds with at least one charged nitrogen atom. Cyclodextrins have a lipophilic center but a hydrophilic outer core, attributable to negatively charged ions on their surface. These negatively charged ions on the surface of Sugammadex attract the positive charges of the quaternary ammonium relaxant, drawing the drug in to the central core of the cyclodextrin. The binding of the guest molecule into the host cyclodextrin occurs because of vander waal's forces, hydrophobic and electrostatic interactions. The structure of the cyclodextrin is such that all four hydrophobic rings of the steroidal relaxant fit tightly within the concentric doughnut forming an inclusion complex. This has been confirmed by calorimetry and X-ray crystallography. Such a reaction occurs in the plasma not at the neuromuscular junction and the concentration of free rocuronium in the plasma decrease rapidly after Sugammadex administration.

U.S. Pat. No. 6,670,340 disclose process for preparation of Sugammadex sodium. The process as disclosed in example 4 of this patent involves reaction of iodo γ-cyclodextrin intermediate with 3-mercapto propionic acid in presence of sodium hydride and DMF to give 6-per-deoxy-6-per-(3-carboxyethyl)thio-γ-cyclodextrin, sodium salt (Sugammadex sodium). The preparation of iodo intermediate, 6-per-deoxy-6-per-iodo-γ-cyclodextrin is as given in example 3 which involves reaction of γ-cyclodextrin with iodine in presence of triphenylphosphine (PPh3) and DMF. In practice, and to develop a process that has to be taken from lab scale to manufacturing scale, purity is one of the most important criteria. Since this process involves use of triphenylphosphine reagent there is formation of triphenylphosphine oxide as a by-product. Removal of triphenylphosphine oxide from the reaction mass is very difficult as it requires repeated washing with the solvent, which leads to inconsistency in yield of final product Sugammadex sodium. Furthermore, the product was dialysed for 36 hours to get pure compound. The dialysis purification is expensive and provides product in lower yield and hence such processes are not feasible and economical at industrial scale.

Another process for preparing the intermediate compound, 6-perdeoxy-6-per-chloro gamma cyclodextrin as disclosed in WO2012025937 involves use of phosphorous halide in particular, phosphorous pentachloride. WO2012025937 also disclose process for preparation of Sugammadex sodium using this intermediate which involves a) reaction of gamma-cyclodextrin with phosphorous pentachloride and dimethylformamide to obtain 6-perdeoxy-6-per-chloro gamma cyclodextrin and b) reaction of 6-perdeoxy-6-per-chloro gamma cyclodextrin with 3-mercapto propionic acid in presence of alkali metal hydrides and an organic solvent to give Sugammadex sodium. Preparation of chloro gamma cyclodextrine intermediate using phosphorous pentachloride is associated with formation of phosphorous impurities during the reaction, which are difficult to remove and also it involves tedious workup procedure.

WO2014125501 discloses preparation of 6-perdeoxy-6-per-chloro gamma cyclodextrin using phosphorous pentachloride (see example 1). The process as given in example 1 of this patent application was repeated by the present inventors. The first step provided yellow to brown mass which lacked the powder form and the flow properties. The mass was pasty at times and difficult to filter. Thus the process was unclean and tedious. Overall, no consistent product was obtained. WO2014125501 also disclose preparation of Sugammadex sodium using this intermediate which involves reaction of 6-perdeoxy-6-per-halo-gamma-cyclodextrin with 3-mercapto propionic acid in presence of alkali metal alkoxide such as sodium methoxide and organic solvent, the drawback of this reaction is that it needs anhydrous conditions for completion of the reaction.

It has been reported that the generation of impurities and obtaining less pure compounds are major concerns with Sugammadex. Applicant Nippon Organon K.K. in their "Report on the Deliberation Results" submitted to Evaluation and Licensing Division, Pharmaceutical and Food Safety Bureau, Ministry of Health, Labour and Welfare, mentions as follows:

For related substances, specifications for 14 different related substances (Related Substance A, Org 48301, Related Substance B, Related Substance D, Related Substance E, Related Substance F, Related Substance G, Related Substance H, Related Substance I, Related Substance J, Related Substance K, Related Substance L, Related Substance M, Related Substance N), other individual related substances, and total related substances have been set. In the course of regulatory review, the specifications limit for 4 different related substances (Related Substance A, Related Substance D, Related Substance F, Related Substance G) have been changed based on the results of batch analyses. For related substances (degradation products), specifications for Related Substance E, Related Substance I, Related Substance C, Related Substance G, Related Substance D, Related Substance K, other individual degradation products, and total degradation products have been established. In the course of regulatory review, a specification for Impurity A which arises in * (hidden part) step has been newly set and the specification limits for individual degradation products have been changed based on the results of batch analyses and stability studies. The cause for change of the colour of the drug product (the light yellow-brown colour darkened) was investigated using liquid chromatography-ultraviolet-visible spectrophotometry (LC-UV/VIS) and liquid chromatography-mass spectrometry (LC-MS), which suggested that trace amounts of varieties of unspecified degradation products (unidentified), instead of a single degradation product, were involved and in addition to * investigated in formulation development, * and * content of the drug substance, * and * during the manufacture of the drug product, and * were considered to affect the color of the drug product. Therefore, * and *** have been included in the drug substance specification and the relevant manufacturing process steps have been improved.

In view of the above it is clear that Sugammadex is not only prone to degradation but traces of degradation impurities affect and change the colour to yellowish brown and makes it unacceptable in quality. Therefore, it is crucial to carefully select the process to prepare pure Sugammadex sodium.

The reported purification techniques for Sugammadex sodium employ column chromatographic and membrane dialysis which are costly and not convenient in large scale operations. Therefore, the reported processes for preparation of Sugammadex sodium as discussed herein are time consuming and not economically and industrially viable. Thus, there exist a need to provide a process of preparation of Sugammadex sodium which is simple, convenient, with easy work up procedure, economically efficient and the one which provides Sugammadex sodium in good yield and high purity.

OBJECT OF THE INVENTION

An object of the present invention is to provide a process for preparation of 6-perdeoxy-6-per-chloro gamma cyclodextrin which is a key intermediate used for preparation of Sugammadex sodium.

Another object of the present invention is to provide process for preparation of Sugammadex sodium.

Another object of the present invention is to provide novel process for preparation of Sugammadex sodium with good yield and high purity.

Another object of the present invention is to provide simple process for preparation of Sugammadex sodium which involves use of reagents which are conveniently used at industrial scale.

SUMMARY OF THE INVENTION

According to an aspect, the present invention provides processes for preparation of 6-perdeoxy-6-per-halo gamma cyclodextrin which is a key intermediate used for preparation of Sugammadex sodium.

According to another aspect, the present invention provides process for preparation of 6-perdeoxy-6-per-chloro gamma cyclodextrin comprising reaction of gamma cyclodextrin with triphosgene in presence of dimethylformamide.

According to another aspect, the present invention provides process for preparation of 6-perdeoxy-6-per-halo gamma cyclodextrin, hereinafter also halo intermediate of Sugammadex using oxalyl halide, such as oxalyl chloride and oxalyl bromide in presence of dimethylformamide. Preferably the halo intermediate is perdeoxy-6-per-chloro gamma cyclodextrin hereinafter also chloro intermediate of Sugammadex.

In another aspect, the present invention provides process for preparation of Sugammadex sodium comprising reaction of 6-perdeoxy-6-per-chloro gamma cyclodextrin with mercapto propanoic acid and sodamide.

In another aspect, the present invention provides process for preparation of Sugammadex comprising reaction of 6-perdeoxy-6-per-chloro gamma cyclodextrin with mercapto propanoic acid and inorganic base such as sodium hydroxide.

In another aspect, the present invention provides process for preparation of Sugammadex comprising a) reacting 3-mercapto propionic acid and potassium hydroxide in presence of dimethylformamide to get a solution of potassium salt of 3-mercapto propionic acid b) treating potassium salt of 3-mercapto propionic acid obtained in step a) with perdeoxy-6-per-halo gamma cyclodextrin to get the product containing potassium salt of acid of Sugammadex c) treating potassium salt of Sugammadex with acid to get corresponding acid of Sugammadex which is treated with inorganic base such as sodium hydroxide to get Sugammadex sodium.

In another aspect, the present invention provides process for preparation of Sugammadex from corresponding acid involving a step having preparation of potassium salt of such acid.

In another aspect, the present invention provides processes for purification Sugammadex sodium.

In another aspect, the present invention provides pure Sugammadex with purity more than 90%, preferably more than 95%.

DETAILED DESCRIPTION OF THE INVENTION

Figure 1:
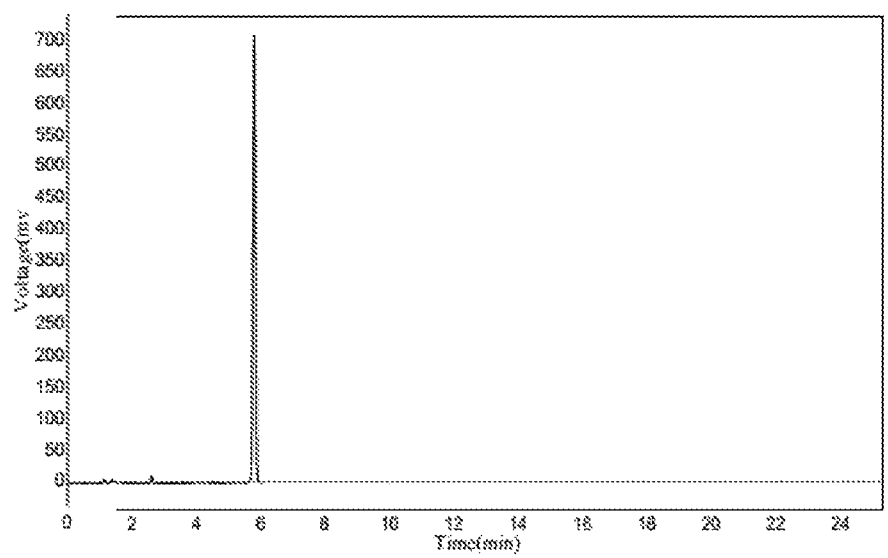
FIG. 1 is HPLC profile of 6-perdeoxy-6-per-chloro gamma cyclodextrin
Figure 2:
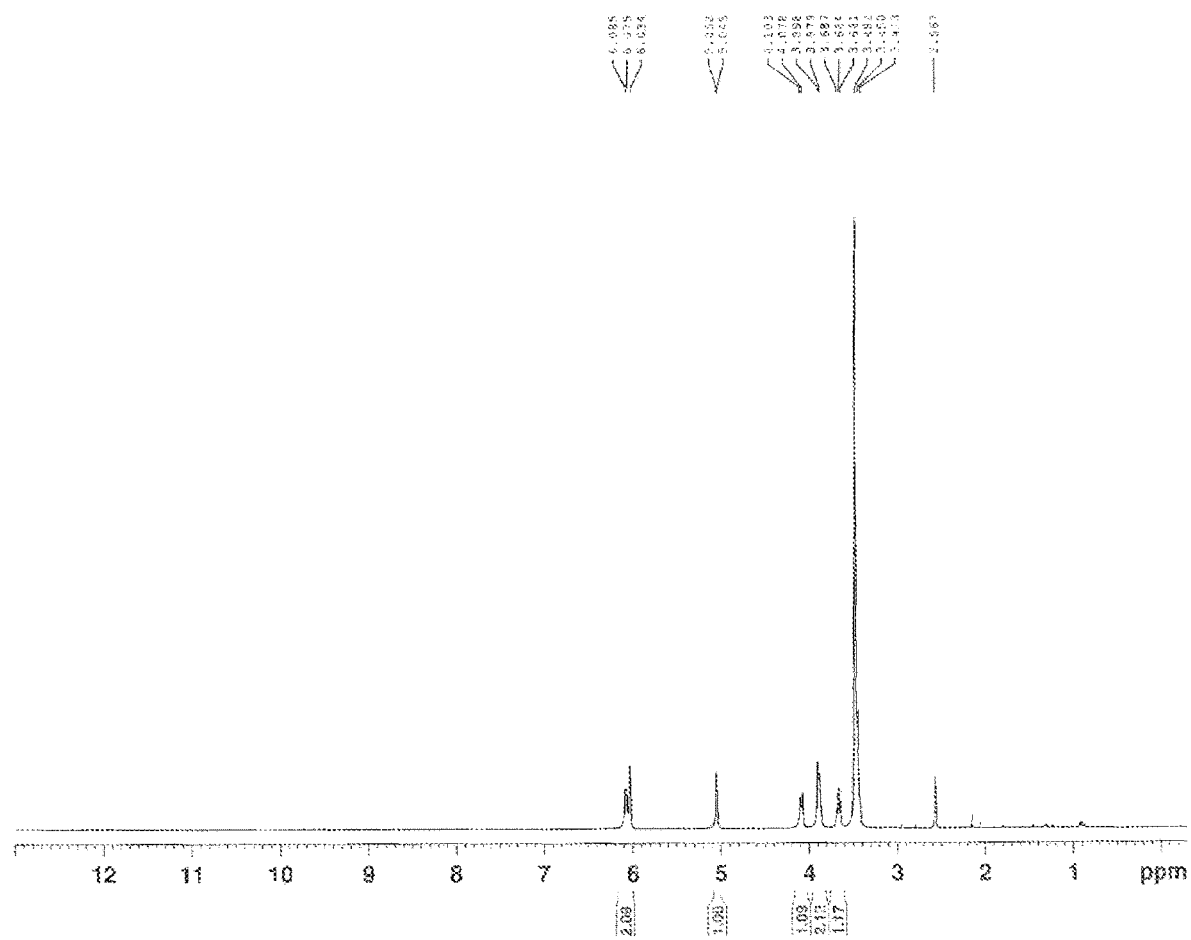
FIG. 2 is 1HNMR of 6-perdeoxy-6-per-chloro gamma cyclodextrin

The present invention provides processes for preparation of halo intermediate of Sugammadex, preferably, chloro intermediate of Sugammadex which is a key intermediate useful in the synthesis of Sugammadex. Further the present invention provides processes for preparation of Sugammadex using this intermediate.

Processes for Preparation of Halo Intermediate

According to first aspect, the present invention provides process for preparation of 6-perdeoxy-6-per-chloro gamma cyclodextrin comprising reaction of gamma cyclodextrin with triphosgene in presence of dimethylformamide to obtain 6-perdeoxy-6-per-chloro gamma cyclodextrin.

According to an embodiment of present invention the reaction of gammacyclodextrin with triphosgene is carried out at temperature in the range of 60-80° C. in presence of dimethylformamide (DMF). The reaction is carried out for 12 to 18 hours. This process is depicted in below scheme 1.

dimethylformamide to obtain halo intermediate of Sugammadex, preferably chloro intermediate of Sugammadex (III).

According to an embodiment reacting gamma-cyclodextrin of formula (II) with oxalyl chloride in presence of

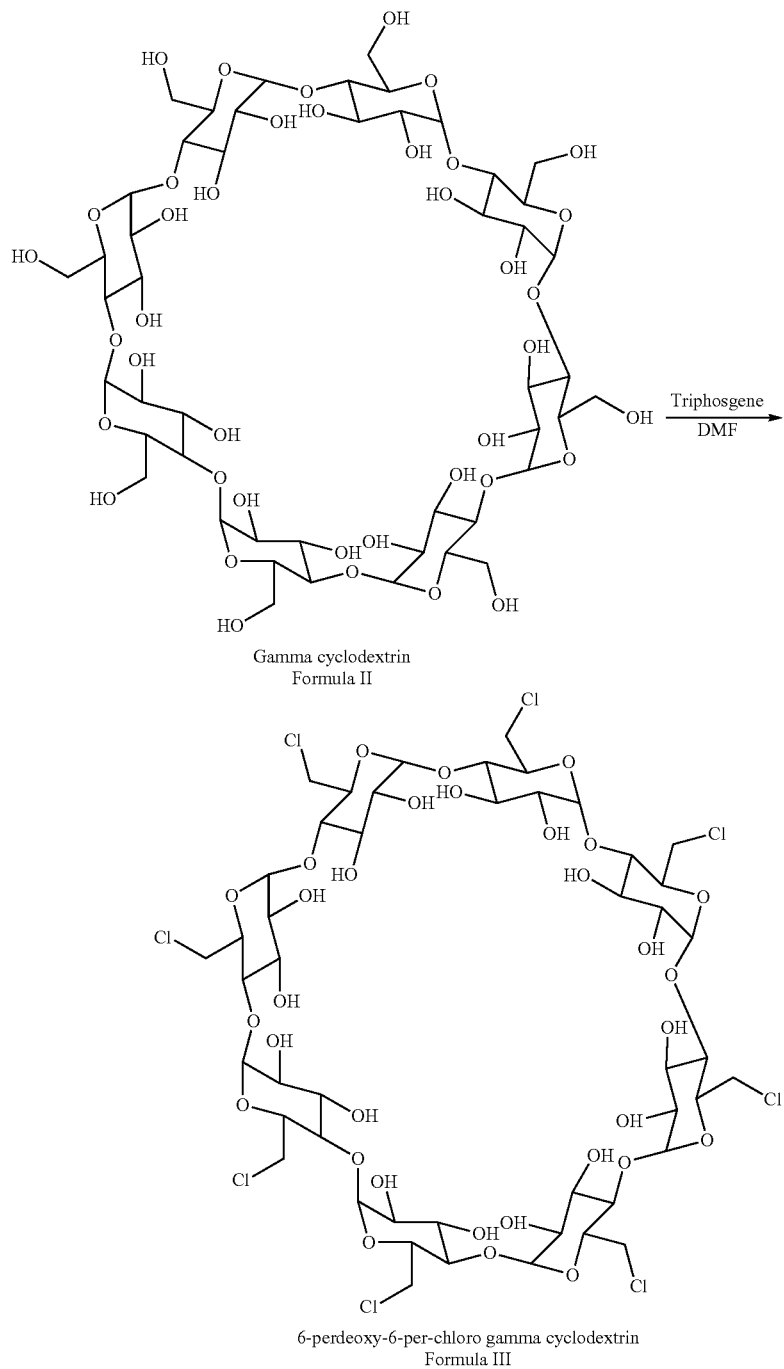

Scheme 1

Gamma cyclodextrin
Formula II 6-perdeoxy-6-per-chloro gamma cyclodextrin
Formula III According to second aspect, the present invention provides a process for preparation of halo intermediate of Sugammadex comprising reacting gamma-cyclodextrin of formula II with oxalyl halide such as oxalyl chloride or oxalyl bromide preferably oxalyl chloride in presence of dimethylformamide (DMF) to obtain chloro intermediate of Sugammadex and optionally purifying chloro intermediate of Sugammadex.

The reaction is performed at temperature in the range of 60-80° C. The reaction is carried out for 12-18 hours.

The purification of perdeoxy-6-per-chloro gamma cyclodextrin involves suspending perdeoxy-6-per-chloro gamma cyclodextrin in alcoholic solvent such as methanol, stirring the suspension and filtering to obtain pure perdeoxy-6-per-chloro gamma cyclodextrin.

The pure perdeoxy-6-per-chloro gamma cyclodextrin obtained according to present invention has purity more than 98%.

This process is depicted in below scheme 2.

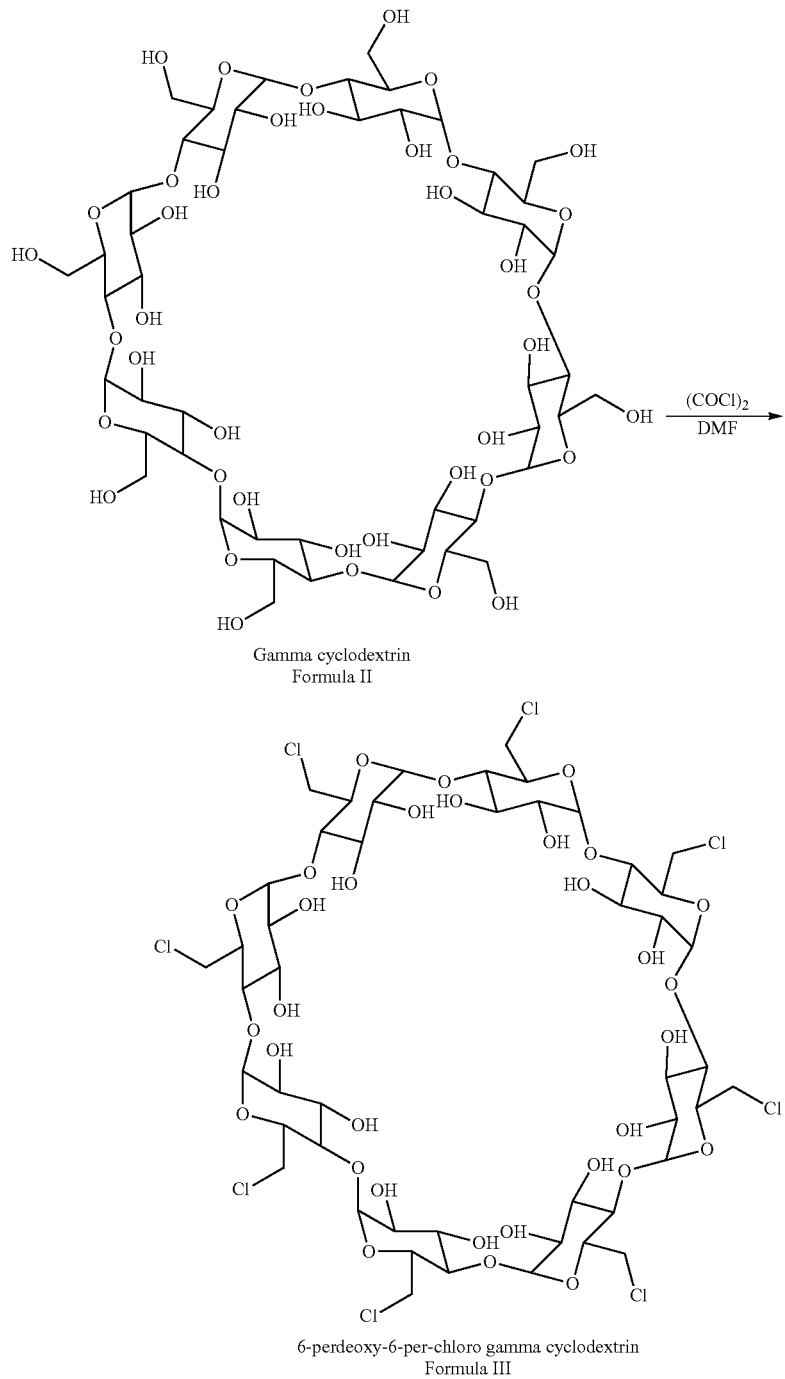

Process for Preparation of Sugammadex Sodium

In third aspect, the present invention provides processes for preparation of Sugammadex sodium.

According to the present invention, pure sugammadex sodium is prepared using a simple and convenient process with simple work up process and avoiding the colored impurities and purification techniques such as column chromatography and dialysis as used in the reported processes.

In an embodiment, the process for preparation of Sugammadex sodium comprising reaction of 6-perdeoxy-6-perchloro gamma cyclodextrin (Formula II) with 3-mercaptopropionic acid in presence of alkali metal amide selected from lithium amide, sodium amide (sodamide) or potassium amide to get Sugammadex sodium.

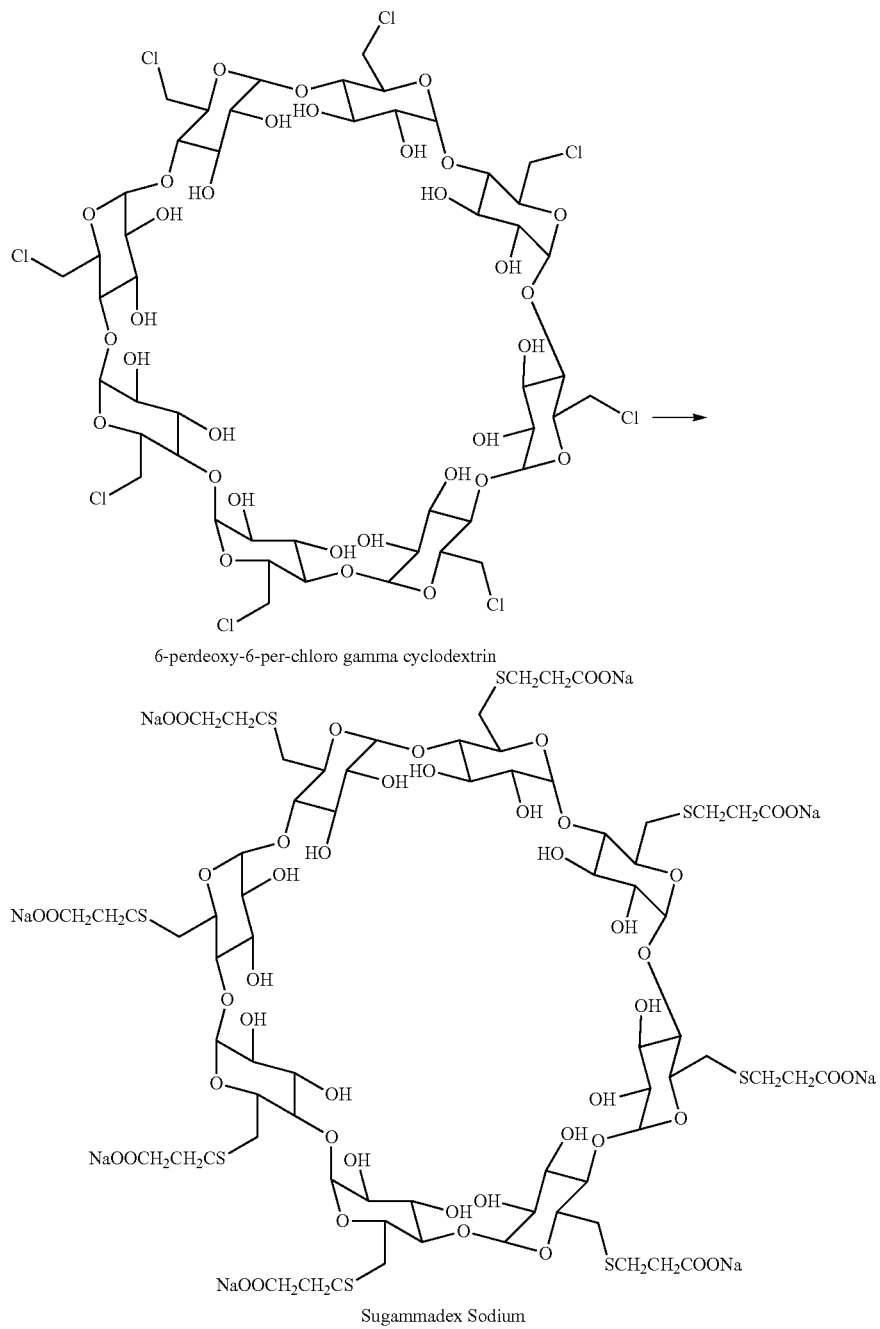

Scheme 3

In an embodiment, the process for preparation of Sugammadex sodium comprising reaction of 6-perdeoxy-6-per-chloro gamma cyclodextrin with 3-mercaptopropionic acid in presence of sodamide to get Sugammadex sodium.

In another embodiment, the process for preparation of Sugammadex sodium comprises:
a) reacting gamma cyclodextrin with triphosgene in presence of dimethylformamide to obtain 6-perdeoxy-6-per-chloro gamma cyclodextrin;
b) reacting 6-perdeoxy-6-per-chloro gamma cyclodextrin with 3-mercaptopropionic acid in presence of alkali metal amide selected from lithium amide, sodium amide (sodamide) or potassium amide to get Sugammadex sodium.

In an embodiment the step a) of the process for preparation of Sugammadex sodium is carried out at temperature in the range of 60-80° C.

In another embodiment the step a) of the process is carried out in presence of dimethylformamide (DMF). In another embodiment the reaction of the step a) of the process is carried out for 12 to 18 hours.

In an embodiment the step b) of the process for preparation of Sugammadex sodium is carried out at temperature in the range of 60-100° C. In another embodiment the reaction of the step b) of the process is carried out for 9 to 18 hours. In another embodiment the step b) of the process is carried out in presence of suitable organic solvent selected from the group consisting of DMF, acetonitrile and dimethylsulfoxide (DMSO).

This process for preparation of Sugammadex sodium is two-step process as described herein.

In the first step, 6-perdeoxy-6-per-chloro gammacyclodextrin is prepared by reacting gamma cyclodextrin with triphosgene in presence of dimethylformamide. Triphosgene has the following advantages in the process of the present invention.
1. It is convenient to handle than phosphorous halides.
2. Use of triphenylphosphine and thereby triphenylphosphine oxide formation as a by-product is avoided thereby making the process industrially viable.
3. It does not require tedious work up process.
4. It gives 6-perdeoxy-6-per-chloro gamma cyclodextrin as white compound as compared to yellowish brown compound obtained in reported processes.
5. The 6-perdeoxy-6-per-chloro gamma cyclodextrin is free flowing powder as compared to pasty (brown) mass of prior art.

In the second step, 6-perdeoxy-6-per-chloro gamma cyclodextrin is reacted with 3-mercapto propionic acid in presence of alkali metal amide selected from lithium amide, sodium amide (sodamide) or potassium amide preferably sodium amide to get Sugammadex sodium.

According to another embodiment, the process for preparation of sugammadex sodium comprises reaction of 6-perdeoxy-6-per-chloro gamma cyclodextrin with 3-mercaptopropionic acid in presence of alkali metal amide selected from lithium amide or potassium amide to get corresponding salt of Sugammadex. The corresponding salt of sugammadex is converted to acid of sugammadex using acid such as hydrochloric acid. The acid of sugammadex is treated with alkali hydroxide such as sodium hydroxide to get sugammadex sodium.

According to another embodiment, the reaction of 6-perdeoxy-6-per-chloro gamma cyclodextrin with 3-mercapto propionic acid is carried out in presence of sodium amide (sodamide) and dimethylformamide.

The main advantage of using sodamide in the process of the present invention is that the production of impurities formed in the reaction is limited and is less than that prepared using bases such as sodium methoxide and sodium hydride. The desired product, Sugammadex sodium is obtained in good yield and high purity of at least 90%. Sugammadex sodium can be purified for example by preparative HPLC to get pure Sugammadex sodium of purity more than 99%.

In another embodiment, the process for preparation of Sugammadex sodium comprising the steps of
a) reacting gammacyclodextrin with triphosgene in presence of dimethylformamide to obtain 6-perdeoxy-6-per-chloro gamma cyclodextrin;
b) reacting 6-perdeoxy-6-per-chloro gamma cyclodextrin with 3-mercaptopropionic acid in presence of alkali metal amide selected from lithium amide, sodium amide (sodamide) or potassium amide and dimethylformamide to get Sugammadex sodium.
c) optionally purifying Sugammadex sodium to get pure Sugammadex sodium.

According to another embodiment, the present invention provides process for preparation of Sugammadex sodium comprising the steps of:
a) reacting gamma-cyclodextrin with triphosgene in presence of dimethylformamide to obtain perdeoxy-6-per-chloro gamma cyclodextrin;
b) reacting perdeoxy-6-per-chloro gamma cyclodextrin with 3-mercapto propionic acid in presence of sodium hydroxide to form Sugammadex sodium;
c) optionally purifying Sugammadex sodium.

According to another embodiment, the present invention provides process for preparation of Sugammadex sodium comprising the steps of:
a) reacting gamma-cyclodextrin with triphosgene in presence of dimethylformamide to obtain perdeoxy-6-per-chloro gamma cyclodextrin;
b) reacting 3-mercapto propionic acid and potassium hydroxide in presence of dimethylformamide to get a solution of potassium salt of 3-mercapto propionic acid
c) treating potassium salt of 3-mercapto propionic acid obtained in step b) with halo intermediate of Sugammadex, preferably chloro intermediate of Sugammadex of formula III to get the product containing potassium salt of acid of Sugammadex.
d) treating the compound of step c) with acid to obtain the compound of formula (IV);
e) reacting the compound of formula (IV) with sodium hydroxide to obtain Sugammadex sodium.
f) optionally purifying Sugammadex sodium.

According to another embodiment the process for preparation of Sugammadex comprising reacting the halo intermediate of Sugammadex, preferably 6-perdeoxy-6-per-chloro gamma cyclodextrin with 3-mercapto propionic acid and sodium hydroxide to obtain Sugammadex of formula (I).

The reaction is carried out in presence of organic solvent selected from the group consisting solvent selected from dimethylformamide (DMF), dimethylacetamide (DMA), N-methyl pyrrolidone (NMP) and dimethylsulfoxide (DMSO).

The reaction is performed at temperature in the range of 70-90° C. for 16-20 hrs. This process is depicted in below scheme 4.

Scheme 4

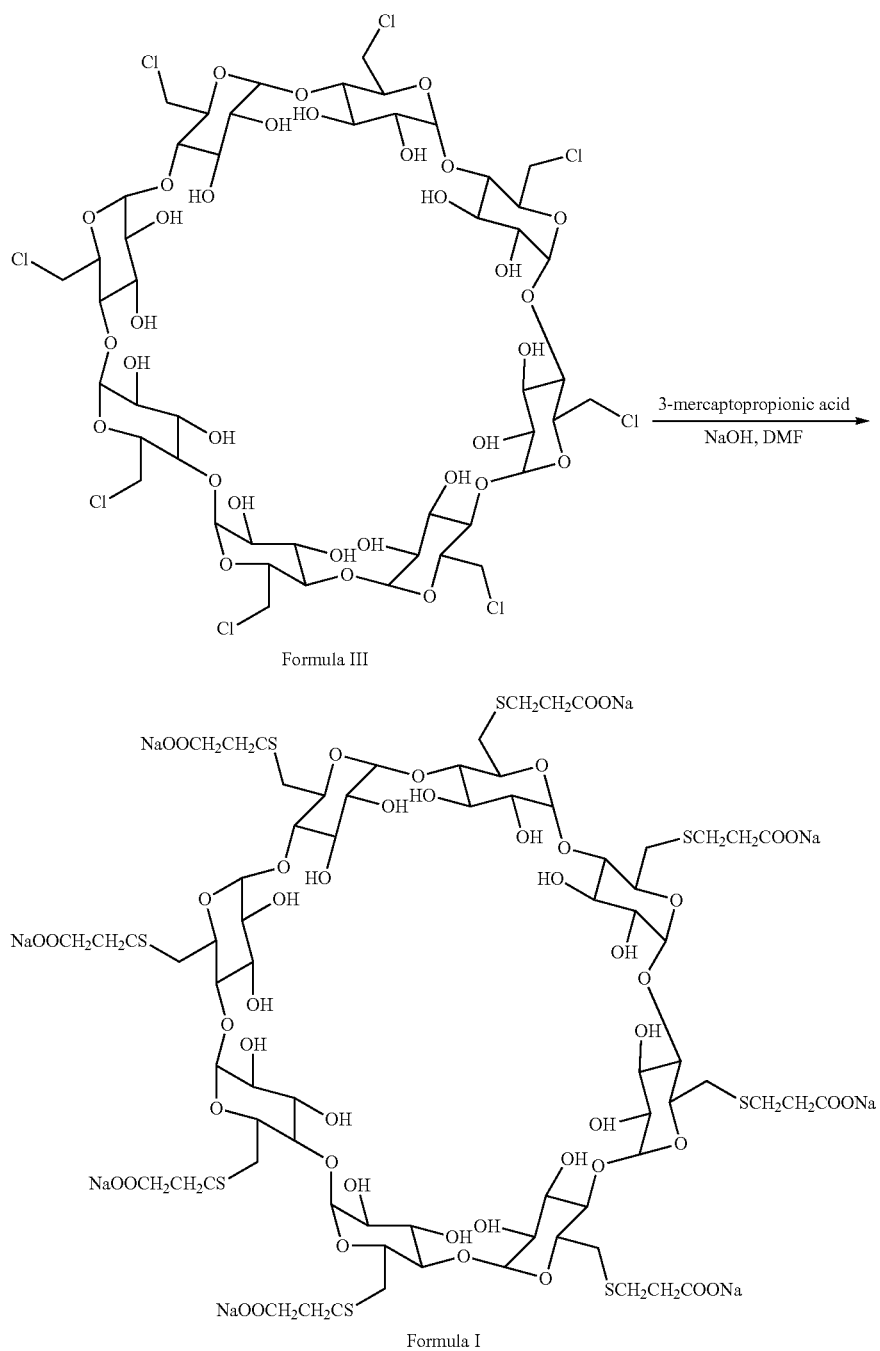

According to another embodiment the present invention provides process for preparation of acid of Sugammadex of formula (IV) comprising a) reacting halo intermediate of Sugammadex, preferably chloro intermediate of Sugammadex of formula III with 3-mercapto propionic acid and potassium hydroxide to get the product containing potassium salt of acid of Sugammadex.

b) treating the compound obtained in step a) with acid to form the compound of formula (IV);

Scheme 5
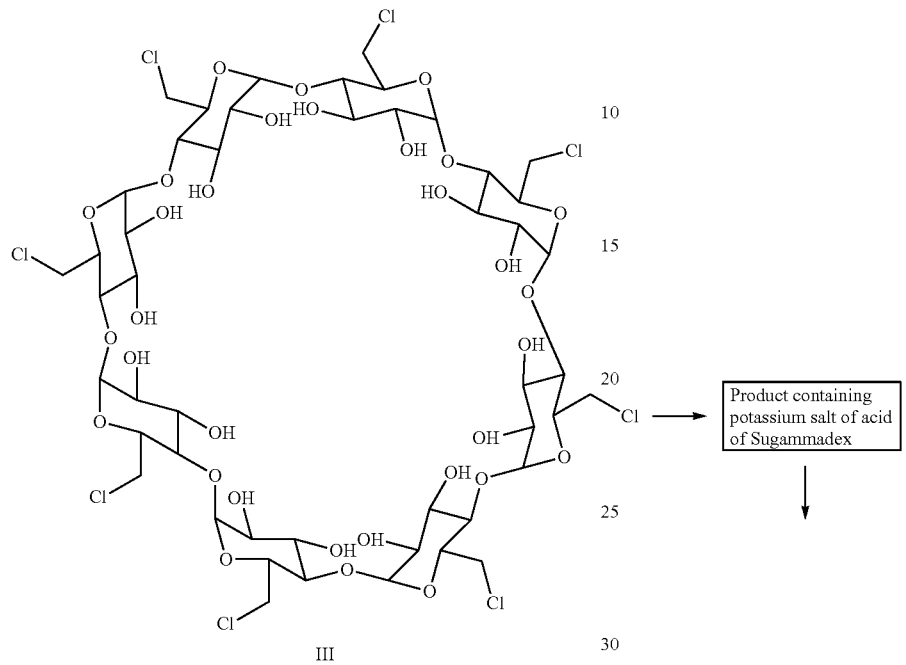
III → Product containing potassium salt of acid of Sugammadex
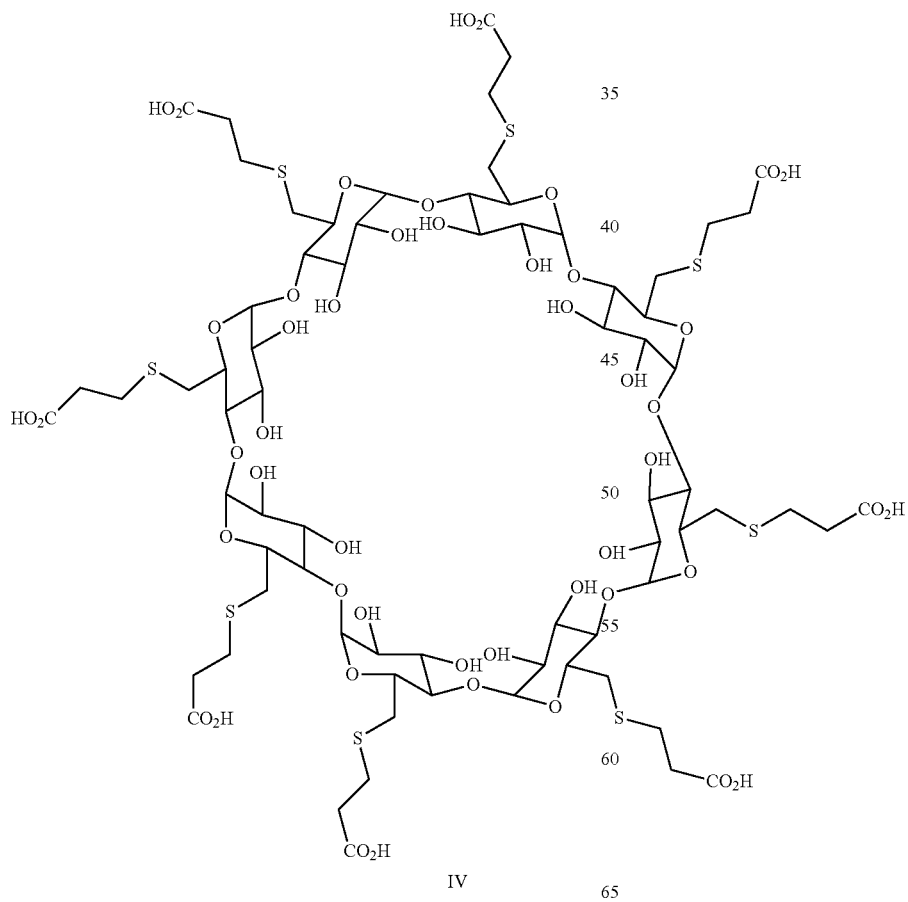
IV According to another embodiment the present invention provides process for preparation of acid of Sugammadex of formula (IV) comprising
a) reacting 3-mercapto propionic acid and potassium hydroxide in presence of dimethylformamide to get a solution of potassium salt of 3-mercapto propionic acid
b) treating potassium salt of 3-mercapto propionic acid obtained in step a) with halo intermediate of Sugammadex, preferably chloro intermediate of Sugammadex of formula III to get the product containing potassium salt of acid of Sugammadex.
c) treating the compound obtained in step b) with acid to form the compound of formula (IV);

According to another embodiment, the present invention provides process for preparation of Sugammadex comprising reacting the acid of Sugammadex of formula (IV) with sodium hydroxide to form Sugammadex sodium of formula (I).

Scheme 6

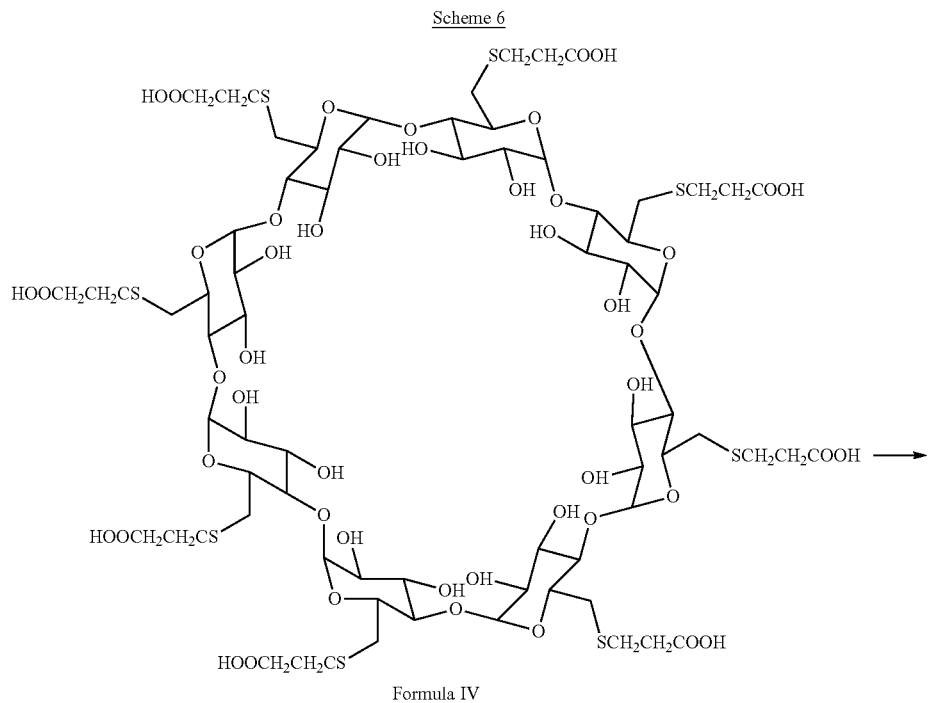

Formula IV

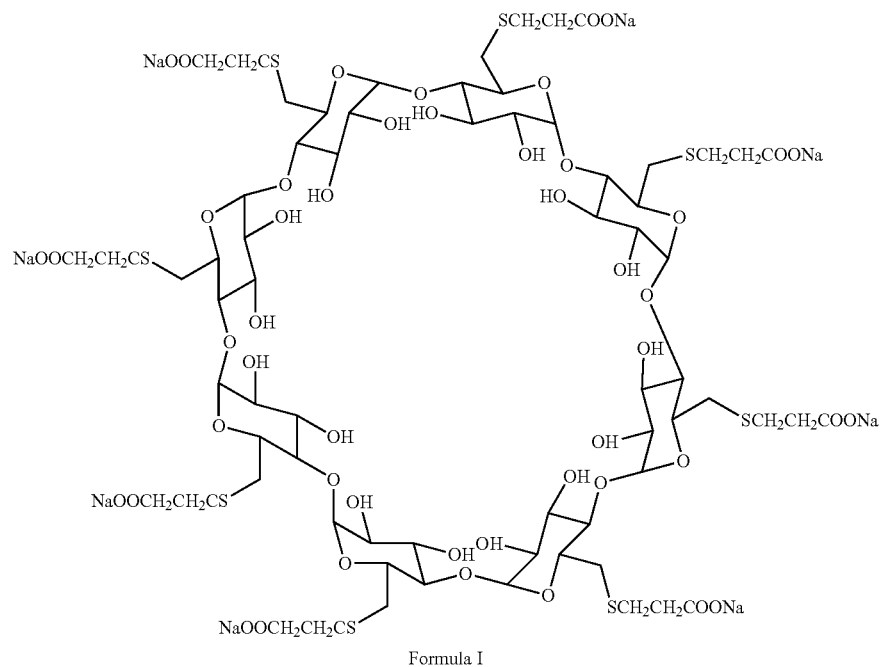

Formula I

The terms 'compound of formula (I) and 'Sugammadex' and 'Sugammadex sodium' are used herein interchangeably and the terms 'compound of formula (IV) and 'Sugammadex acid' and acid of Sugammadex are used herein interchangeably.

The compound, 6-perdeoxy-6-per-halo gamma cyclodextrin and halo intermediate of Sugammadex are used herein interchangeably.

6-perdeoxy-6-per-chloro gamma cyclodextrin and chloro intermediate of Sugammadex are used herein interchangeably.

According to another embodiment the process for preparation of Sugammadex sodium comprises
a) reacting gamma-cyclodextrin with triphosgene or oxalyl chloride in presence of DMF at temperature in the range of 60-80° C. for 12-18 hr to obtain chloro intermediate of Sugammadex;
b) converting chloro intermediate of Sugammadex to Sugammadex sodium.

According to another embodiment of the present invention, the conversion of chloro intermediate of Sugammadex, 6-perdeoxy-6-per-chloro gamma cyclodextrin into Sugammadex sodium comprises reacting 6-perdeoxy-6-per-chloro gamma cyclodextrin with 3-mercapto propionic acid in presence of sodium hydroxide to obtain Sugammadex sodium;
OR
reacting 6-perdeoxy-6-per-chloro gamma cyclodextrin with 3-mercaptopropionic acid in presence of alkali metal amide selected from lithium amide, sodium amide (sodamide) or potassium amide to get Sugammadex
OR
(a) reacting 3-mercapto propionic acid and potassium hydroxide in presence of dimethylformamide to get a solution of potassium salt of 3-mercapto propionic acid
(b) treating potassium salt of 3-mercapto propionic acid obtained in step a) with halo intermediate of Sugammadex, preferably chloro intermediate of Sugammadex of formula III to get the product containing potassium salt of acid of Sugammadex.
(c) treating the product obtained in step b) with acid to obtain the compound of formula (IV);
(d) reacting the compound of formula (IV) with sodium hydroxide to obtain Sugammadex sodium of formula (I).

In another embodiment, the process for preparation of Sugammadex sodium comprises:
a) reacting gamma cyclodextrin with oxalyl chloride in presence of dimethylformamide to obtain 6-perdeoxy-6-per-chloro gamma cyclodextrin;
b) reacting 6-perdeoxy-6-per-chloro gamma cyclodextrin with 3-mercaptopropionic acid in presence of alkali metal amide selected from lithium amide, sodium amide (sodamide) or potassium amide to get Sugammadex sodium.

In an embodiment the step a) of the process is carried out at temperature in the range of 60-80° C. In another embodiment the step a) of the process is carried out for 12 to 18 hours.

In an embodiment the step b) of the process is carried out at temperature in the range of 60-100° C. In another embodiment the reaction of the step b) of the process is carried out for 9 to 18 hours. In another embodiment the step b) of the process is carried out in presence of suitable organic solvent selected from the group consisting of DMF, acetonitrile and dimethylsulfoxide (DMSO).

In an embodiment the step b) of the process comprises reaction of 6-perdeoxy-6-per-chloro gamma cyclodextrin with 3-mercaptopropionic acid in presence of sodium amide (sodamide) to get Sugammadex sodium.

In an embodiment the step b) of the process comprises reaction of 6-perdeoxy-6-per-chloro gamma cyclodextrin with 3-mercaptopropionic acid in presence lithium amide or potassium amide to get corresponding salt of Sugammadex and converting the obtained salt to acid of Sugammadex using acid such as hydrochloric acid and treating the obtained acid of Sugammadex with alkali hydroxide such as sodium hydroxide to get Sugammadex sodium.

According to another embodiment, the present invention provides process for preparation of Sugammadex sodium comprising the steps of:
a) reacting gamma-cyclodextrin with triphosgene or oxalyl chloride in presence of dimethylformamide to obtain perdeoxy-6-per-chloro gamma cyclodextrin;
b) reacting perdeoxy-6-per-chloro gamma cyclodextrin with 3-mercapto propionic acid in presence of sodium hydroxide to form Sugammadex sodium;
c) optionally purifying Sugammadex sodium.

The reaction of step a) is performed at temperature in the range of 60-80° C.

The reaction of step a) is carried out for 12-18 hours.

The reaction of step b) is carried out in presence of organic solvent selected from the group consisting of dimethylformamide (DMF), dimethylacetamide (DMA), N-methyl pyrrolidone (NMP) and dimethylsulfoxide (DMSO).

The reaction of step b) is performed at temperature in the range of 70-90° C.

The reaction of step b) is carried out for 16-20 hours.

The purification of Sugammadex in step c) involves the following steps;
1) dissolving Sugammadex sodium in first solvent to obtain a solution
2) treating the solution obtained with activated carbon
3) filtering the solution of step ii) and separating the filtrate and
4) adding second solvent to the filtrate of step iii) to get pure Sugammadex sodium.

The first solvent used in the purification process is selected from the group consisting of water, acetone, DMF, alcohol such as methanol, ethanol and isopropanol and/or mixtures thereof.

The second solvent used in the purification process is selected from acetone, methanol, acetonitrile or mixtures thereof.

The purification step is carried out at temperature in the range of 50-80° C. Sugammadex sodium obtained by this purification has purity more than 90%.

In an alternative method Sugammadex is purified by preparative HPLC method. In an embodiment purification of Sugammadex by preparative HPLC method comprise use of acid of Sugammadex for purification of Sugammadex.

This process for preparation of Sugammadex sodium is illustrated by the following reaction scheme 7.

Scheme 7
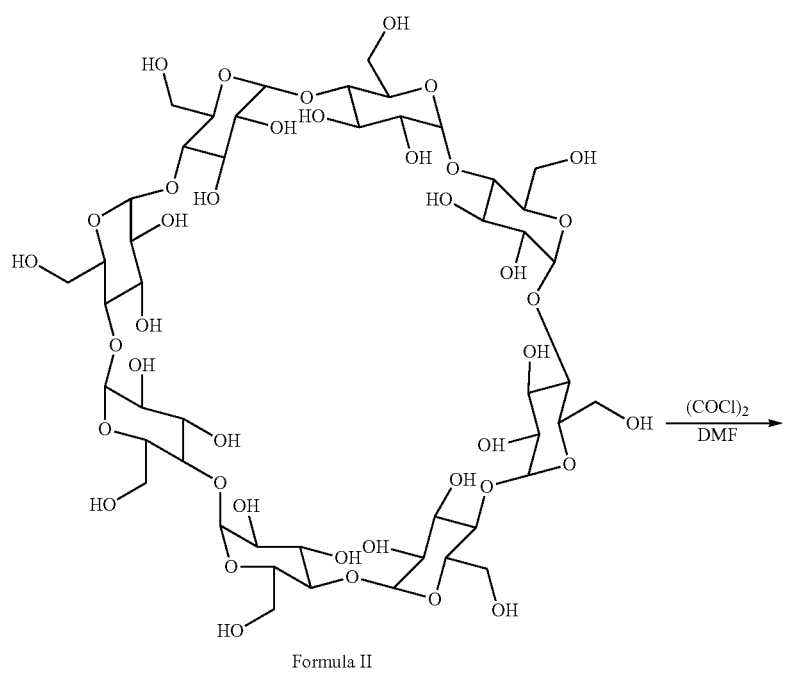
Formula II
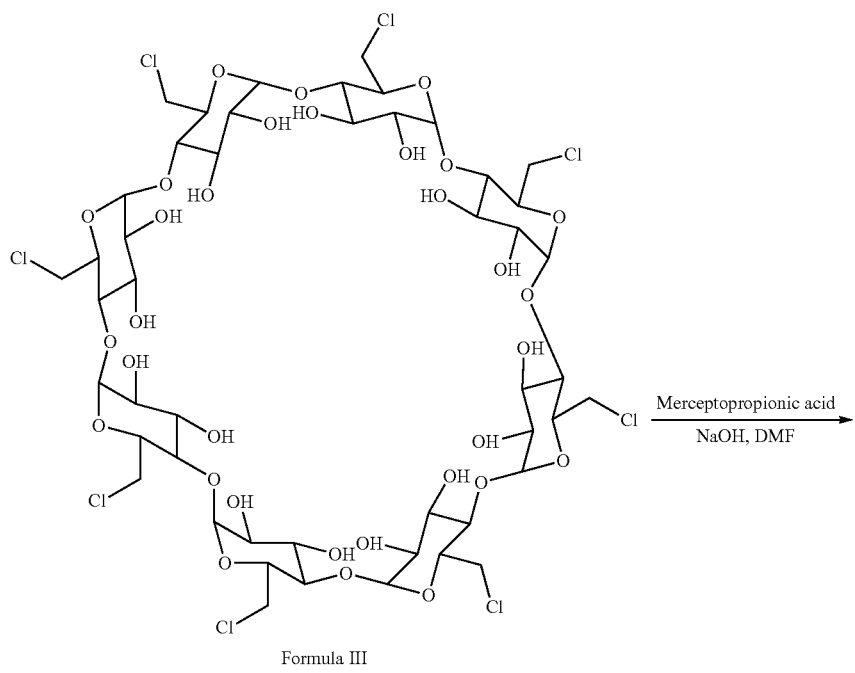
Formula III

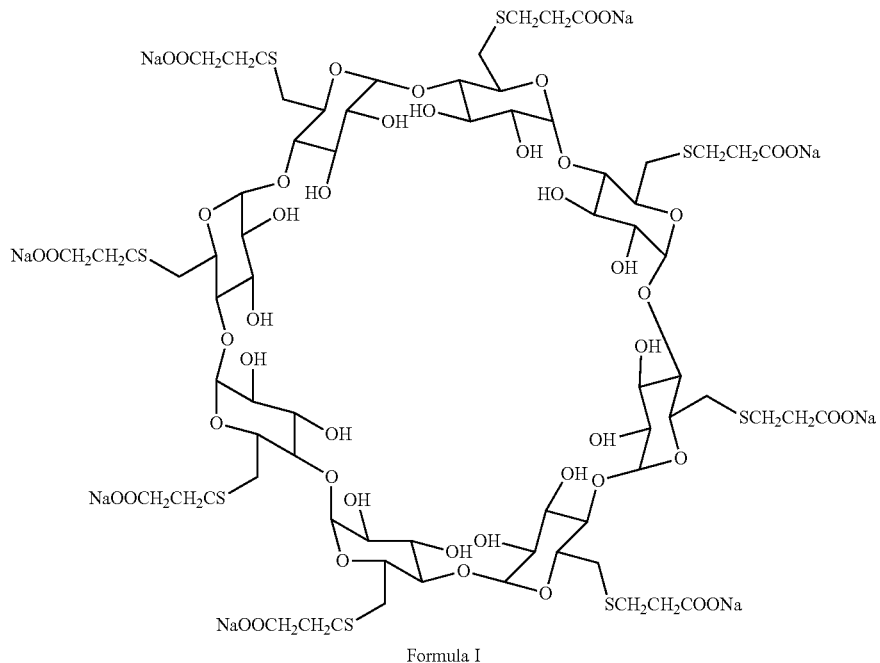

Formula I

According to another embodiment, the present invention provides process for preparation of Sugammadex sodium comprising the steps of
a) reacting gamma-cyclodextrin with oxalyl chloride in presence of dimethylformamide to obtain chloro derivative of Sugammadex of formula (III);
b) reacting 3-mercapto propionic acid and potassium hydroxide in presence of dimethylformamide to get a solution of potassium salt of 3-mercapto propionic acid
c) treating potassium salt of 3-mercapto propionic acid obtained in step b) with halo intermediate of Sugammadex, preferably chloro intermediate of Sugammadex of formula III to get the product containing potassium salt of acid of Sugammadex.
d) treating the product of step c) with acid to obtain the compound of formula (IV);
e) treating the compound of formula (IV) with sodium hydroxide to obtain Sugammadex sodium.

The reaction of step a) is performed at temperature in the range of 60-80° C. The reaction of step a) is carried out for 12-18 hours.

The reaction of step b) can be carried out in presence of organic solvent selected from dimethylformamide (DMF), dimethylacetamide (DMA), N-methyl pyrrolidone.(NMP) and dimethylsulfoxide (DMSO).

The reaction of step b) is carried out at 0-10° C. preferably 0-5° C.

In the reaction of step b) and c) halo intermediate compound and mercapto propionic acid and halo intermediate compound and potassium hydroxide are used in a molar ratio of at least 1:15 and at least 1:30 respectively, preferably at least 1:20 and 1:40 respectively and most preferably at least 1:25 and at least 1:50 respectively. The ratio of mercapto propionic acid and potassium hydroxide is about x:y preferably 1:2.

The reaction of step c) is performed at temperature in the range of 80-140° C., preferably at temperature from 110-120° C. The reaction of step c) is carried out for 2 to 6 hr, preferably for 1.5-2 hr.

The acid used in step d) is hydrochloric acid. The reaction of step c) is performed at temperature from 25-35° C. The reaction of step d) is carried out for 1.5-2 hr.

The reaction of step e) is performed at temperature in the range of 25-35° C. The reaction of step e) is carried out 0.5-2 hrs. The process is as depicted in scheme 8.

Scheme 8
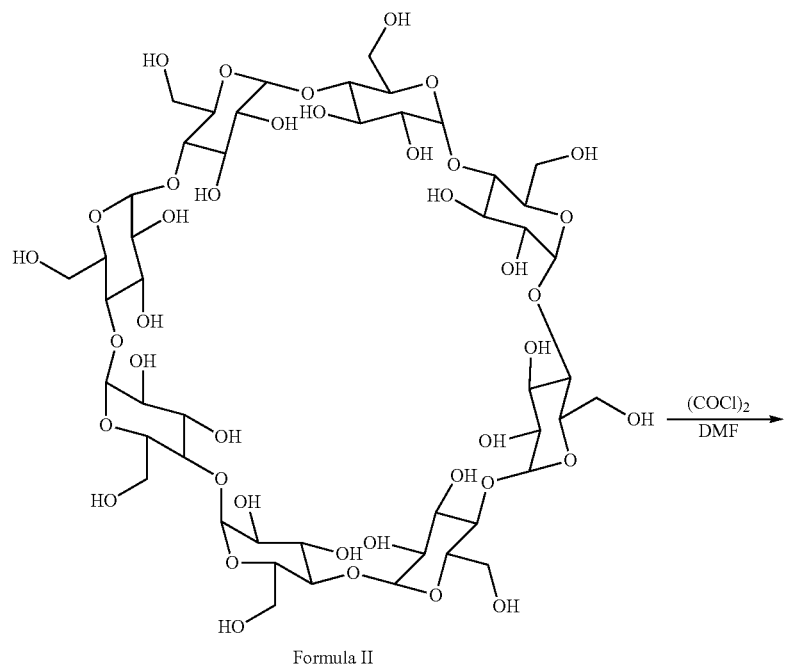
Formula II
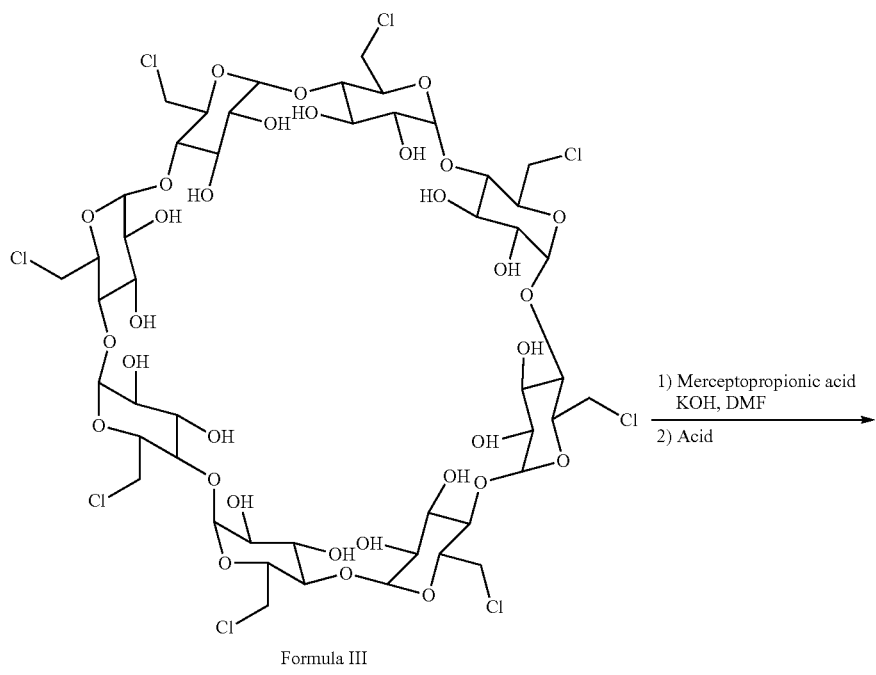
Formula III

-continued

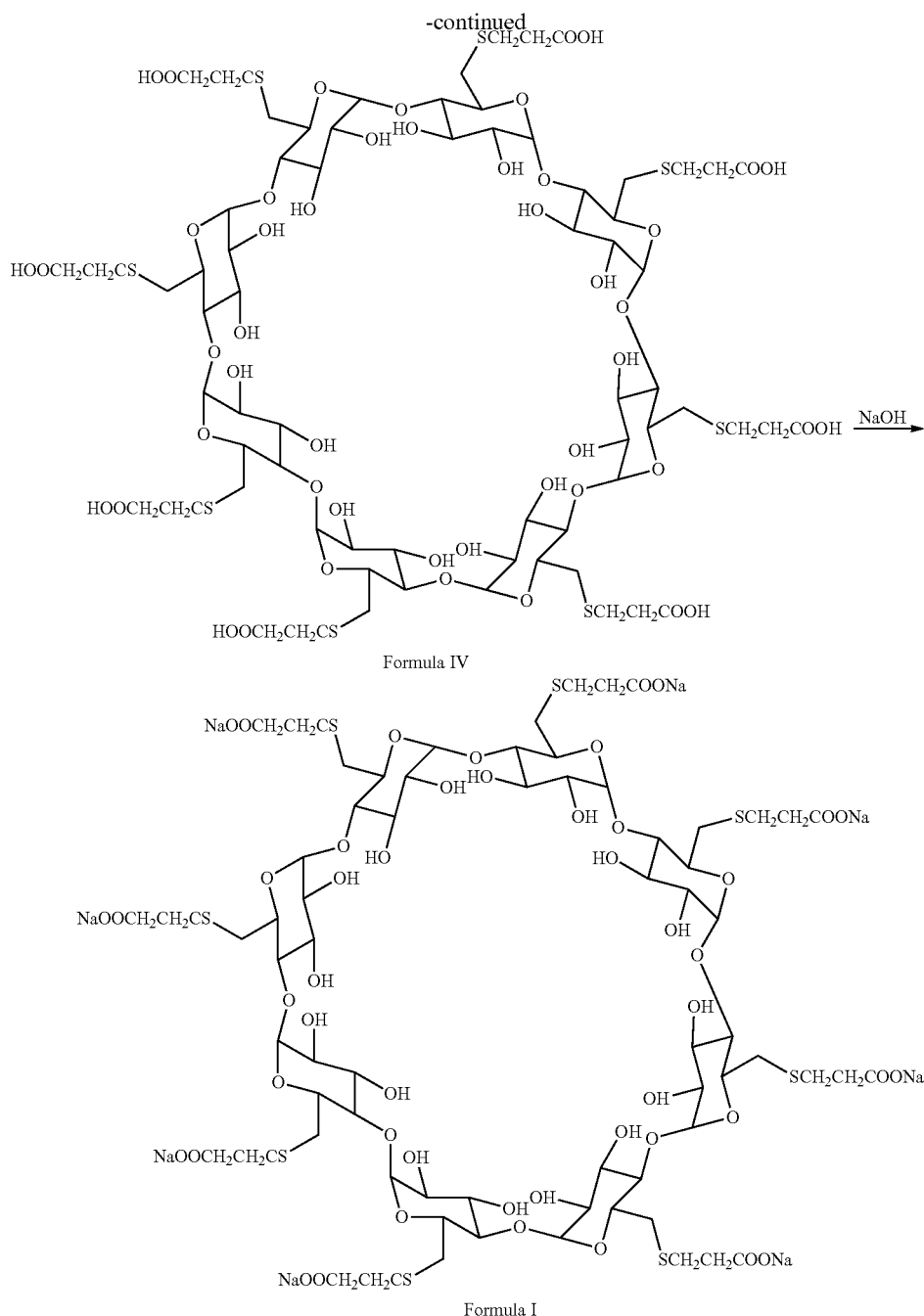

Formula IV

Formula I

The process of preparation of Sugammadex sodium according to above scheme 8 involves the following steps;

Step 1:

In this step a mixture of anhydrous dimethylformamide (DMF) and oxalyl chloride is stirred for 1 hr at temperature below 5° C. and a solution of dry gamma-cyclodextrin dissolved in DMF is added slowly into this mixture. The solution is heated at 65-70° C. for 16 hrs. After the completion of reaction, the reaction mixture is cooled to room temperature and solvent such as diisopropyl ether is added to the reaction mixture with stirring. The solvent is removed and the precipitated gummy solid so obtained is cooled to 0 to 5° C. and neutralized to about pH 8 with slow addition of aqueous sodium hydroxide solution. The reaction mass is stirred for 1 hr at temperature 0 to 5° C. and the precipitated material is filtered, washed with the water. The residue is then suspended into solvent such as methanol, stirred, filtered, washed with solvent such as diisopropyl ether and dried to give 6-deoxy-6-chloro gamma cyclodextrin.

Step 2

In this step a solution of potassium hydroxide in solvent such as DMF is cooled at 0-5° C. and to this a solution of 3-mercapto propionic acid in solvent such as DMF is added maintaining the temperature of reaction mixture between 0-5° C. The reaction mixture is then stirred at this temperature for about 60 minutes to get a clear solution of potassium salt of 3-mercapto propionic acid. Treating the clear solution containing potassium salt of 3-mercapto propionic acid with a solution of 6-deoxy-6-chloro gamma cyclodextrin in DMF. The mixture is heated at about 110-120° C. for about 2 hr. After completion of the reaction, the reaction mixture is cooled to about 40-50° C. and diluted with solvent such as methanol. The resulting precipitate is stirred at 20-25° C. for about 1 hr and filtered under vacuum. The wet solid is then dissolved in water with vigorous stirring and acidified with acid such as concentrated hydrochloric acid (HCl). The precipitated solid of Sugammadex acid is filtered and suspended in solvent such as ethyl acetate, stirred for 30 minutes, filtered and dried. Sugammadex acid obtained has purity more than 95% as measured by HPLC.

Step 3

In this step the compound, Sugammadex acid is dissolved in a solution of sodium hydroxide in a mixture of solvent, preferably water and methanol. The pH of reaction mixture is maintained between 8-10 and anti-solvent such as methanol is added to the mixture. The precipitated solid of Sugammadex sodium is filtered, washed with solvent such as methanol and dried at 50° C. under vacuum oven.

According to another embodiment, the present invention provides process for preparation of Sugammadex sodium comprising the steps of a) reacting chloro derivative of Sugammadex of formula (III) with 3-mercapto propionic acid in presence of potassium hydroxide to give a product containing the potassium salt of acid of Sugammadex;

b) treating the compound of step b) with acid to obtain the compound of formula (IV);

c) reacting the compound of formula (IV) with sodium hydroxide to obtain Sugammadex sodium.

According to another embodiment, the present invention provides process for preparation of Sugammadex sodium comprising treating the compound of formula (IV) with a solution of sodium hydroxide at temperature from 25-35° C. to obtain a solution and precipitating pure Sugammadex sodium using organic solvent. The solution of sodium hydroxide is prepared by dissolving sodium hydroxide in a mixture of solvent. The mixture of solvent used is water and methanol. The solution of sodium hydroxide is added in such an amount that the pH of the reaction is maintained between 8-10. The organic solvent used for precipitation of sodium salt of Sugammadex is selected from methanol, ethanol, isopropanol etc. or mixtures thereof. This process is depicted in below scheme 9.

Scheme 9

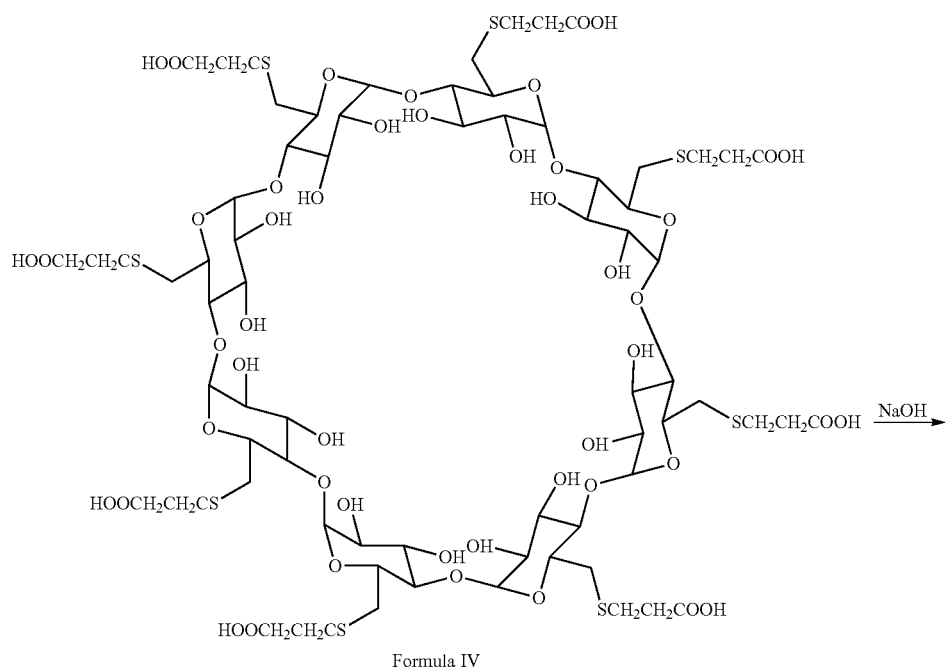

Formula IV

-continued

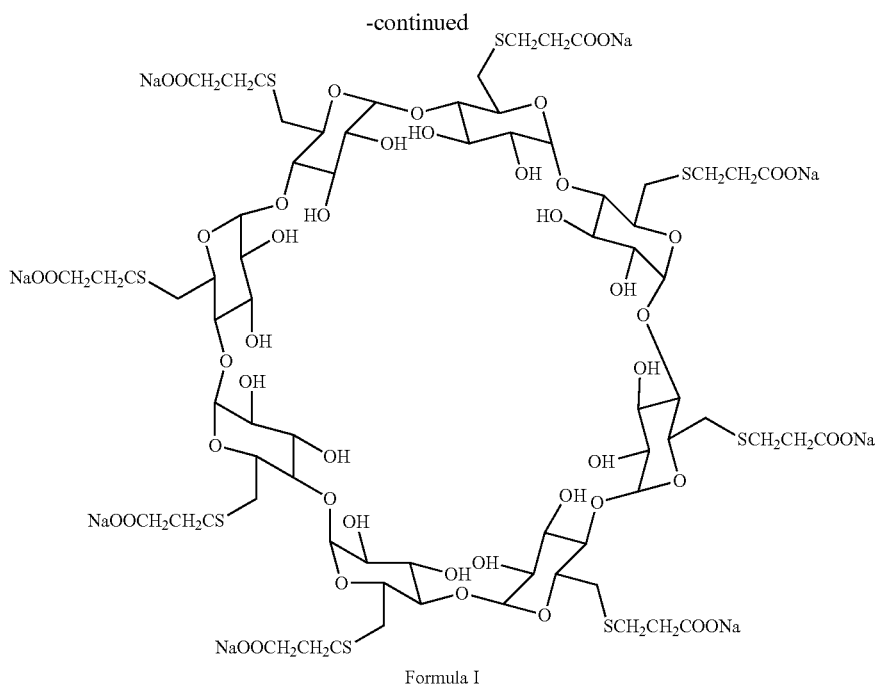

Formula I

Sugammadex sodium prepared according to the present invention is characterized by HPLC profile representing high purity more than 90%, preferably more than 95%.

According to the present invention, pure Sugammadex sodium is prepared using a simple and convenient process with simple work up process and avoiding the formation of by-product/impurities and purification techniques such as column chromatography and dialysis as used in the reported processes.

As it has been discussed that applicant Nippon Organon K.K. reported 14 different related substances for Sugammadex from A to N. Also it is stated that traces of impurities may remain in the product which may result in yellow to brown colored product. The colored impurities cannot be washed out with simple washings. It requires special techniques such as purification by column chromatography or dialysis or some tedious work up processes. The inventors of the present invention followed the reported processes and found that the desired product with high purity could not be achieved. In fact, it is very tricky to obtain pure and white desired product.

The inventors of the present invention found that it was easy to handle the large scale operations when they used oxalyl halide such as oxalyl chloride and oxalyl bromide to prepare the halo intermediate, perdeoxy-6-per-halo gamma cyclodextrin preferably perdeoxy-6-per-chloro gamma cyclodextrin and sodium hydroxide for the preparation of Sugammadex from 6-perdeoxy-6-per-halo gamma cyclodextrin. The resulted reaction mixture in such reaction was easy for work up after the completion of the reaction.

The process of the present invention is convenient as oxalyl chloride is used instead of reported phosphorous pentachloride ($PCl_5$), triphenylphosphine (PPh3) and provides a white pure solid which gives upon drying white free flowing material as compared to yellow to brown pasty compound which is obtained when inventors of present invention repeated the process disclosed in WO2014125501.

The process of the present invention provides pure Sugammadex sodium using sodium hydroxide than reported bases such as sodium hydride and sodium methoxide used for making Sugammadex sodium.

Interestingly, none of the WO2014125501 and WO2012025937 mentions about different impurities present in the final product Sugammadex sodium prepared under the respective process.

Purification of Sugammadex Sodium

Sugammadex sodium prepared according to the present invention is characterized by HPLC profile representing high purity more than 95%.

The formation of the reaction products is monitored by HPLC. Sugammadex sodium prepared according to the present invention is subjected to purification preferably preparative HPLC to get pure Sugammadex sodium having more than 95% HPLC purity, preferably more than 98%.

The purification techniques in the prior arts employ column chromatographic/membrane dialysis techniques which are costly and not convenient in large scale operations. The process of the present invention further provides Sugammadex sodium with high purity.

According to an aspect the present invention provides process for purification of sugammadex sodium.

In an embodiment, Sugammadex sodium is purified by the preparative HPLC method using formic acid buffer in mixture of acetonitrile and water. Finally, the lyophilization of the desired fraction gave Sugammadex sodium of purity more than 99%.

According to another embodiment, Sugammadex sodium is purified by dissolving the crude product in suitable solvent selected from the group consisting of water, acetone, DMF, alcohol such as methanol, ethanol and isopropanol and/or mixtures thereof followed by addition of activated charcoal. The solution obtained is stirred for about 30 min and filtered. The product is precipitated out from the filtrate using suitable solvent selected from acetone, methanol, acetonitrile or mixtures thereof to get Sugammadex sodium having purity more than 90%, preferably more than 95%.

Figure 3:
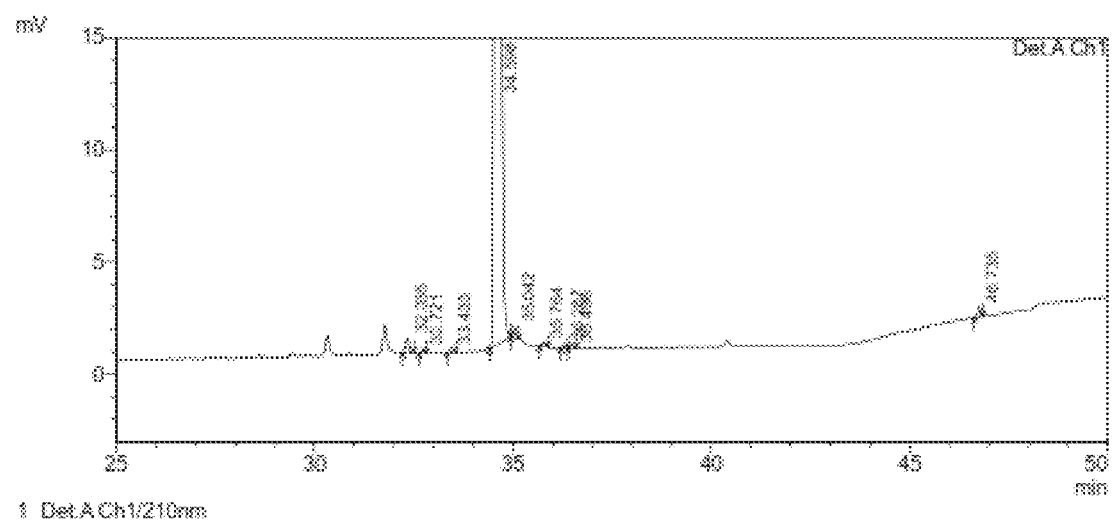
FIG. 3 is HPLC profile of Sugammadex sodium having purity more than 99%
Figure 4:
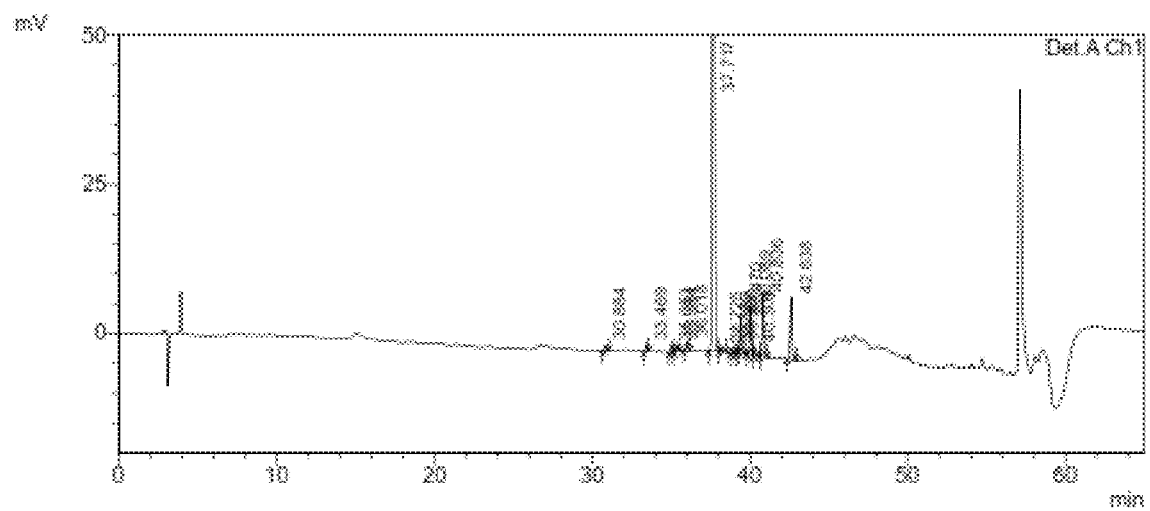
FIG. 4 is HPLC profile of Sugammadex sodium prepared according to example 5
Figure 5:
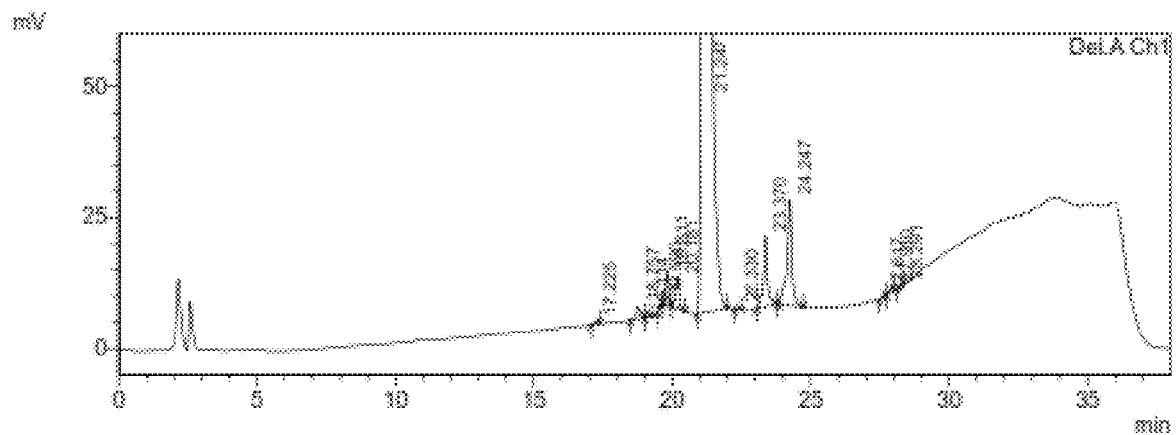
FIG. 5 is HPLC profile of Sugammadex sodium prepared according to example 6
Figure 6:
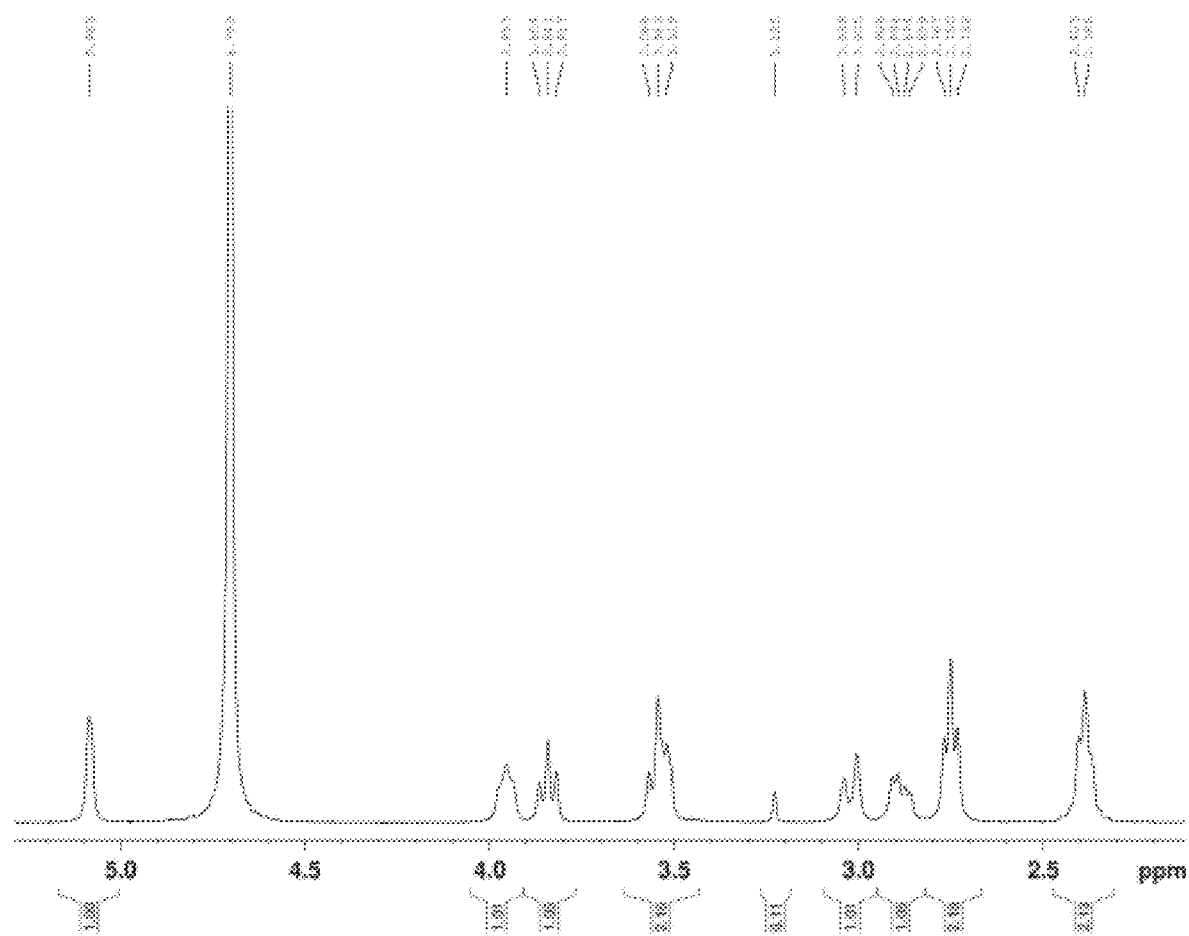
FIG. 6 is 1HNMR of Sugammadex prepared according to example 6
Figure 7:
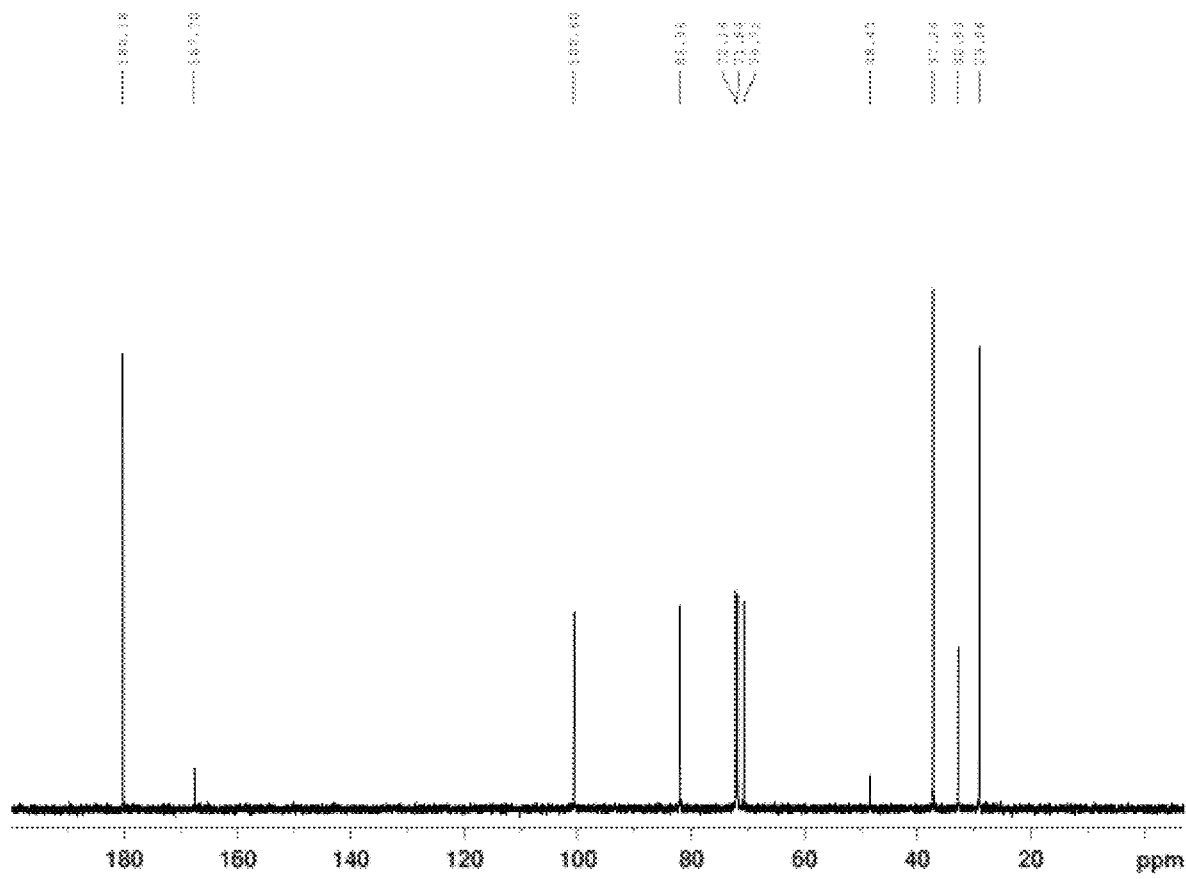
FIG. 7 is 13CNMR of Sugammadex prepared according to example 6
Figure 8:
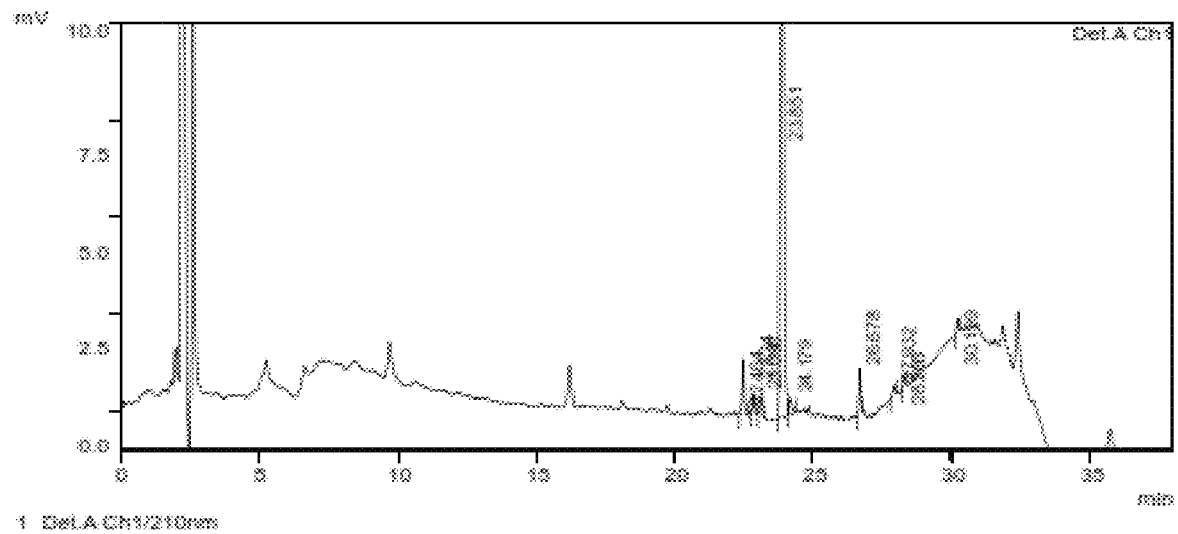
FIG. 8 is HPLC profile of Sugammadex acid (compound of formula IV)
Figure 9:
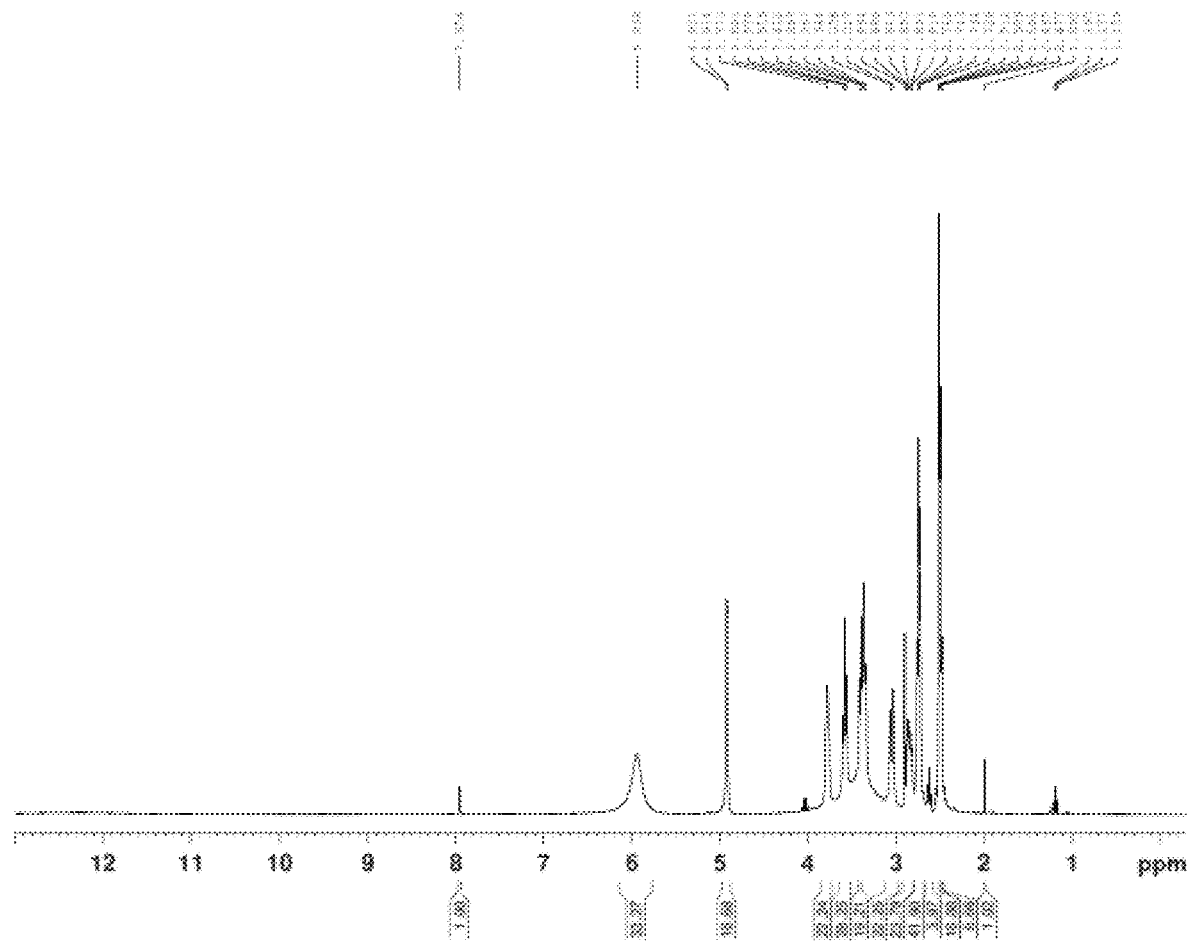
FIG. 9 is 1HNMR of compound of formula IV
Figure 10:
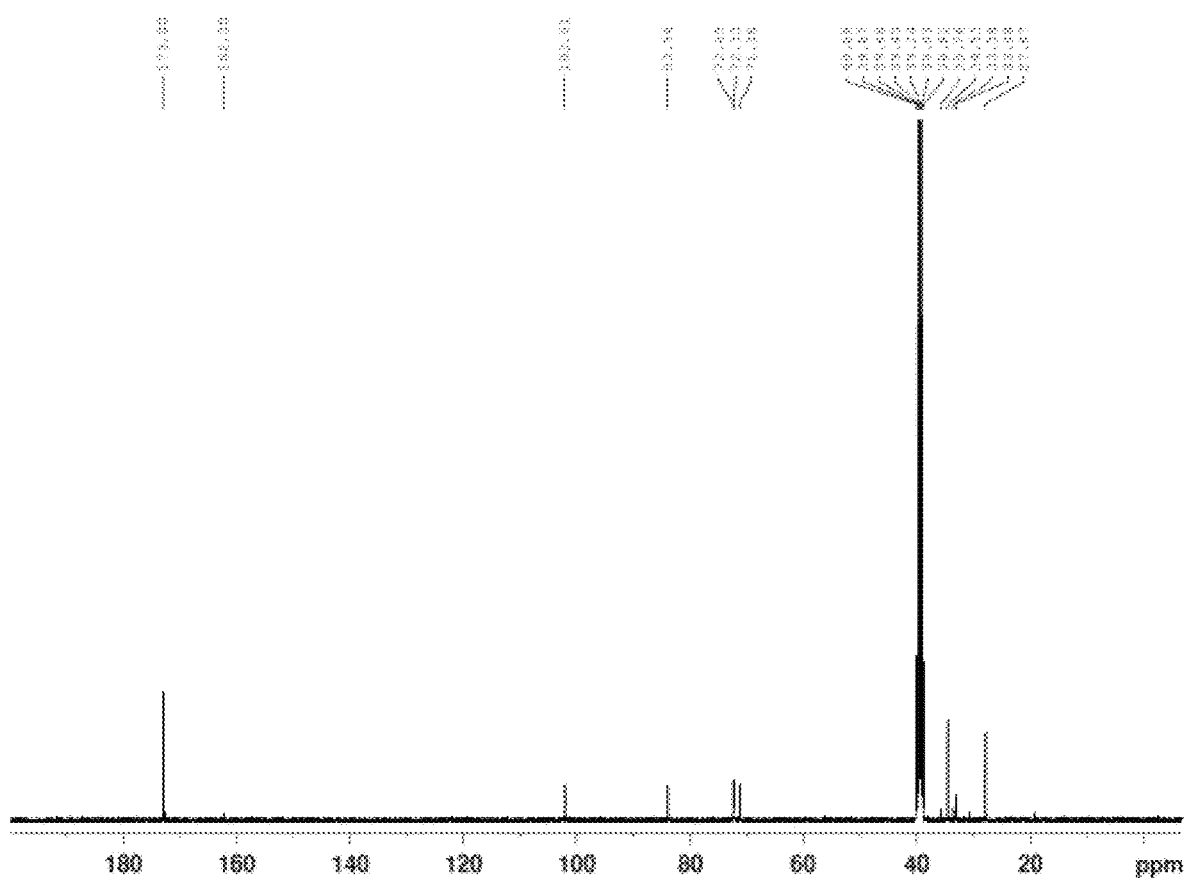
FIG. 10 is 13CNMR of compound of formula IV
Figure 11:
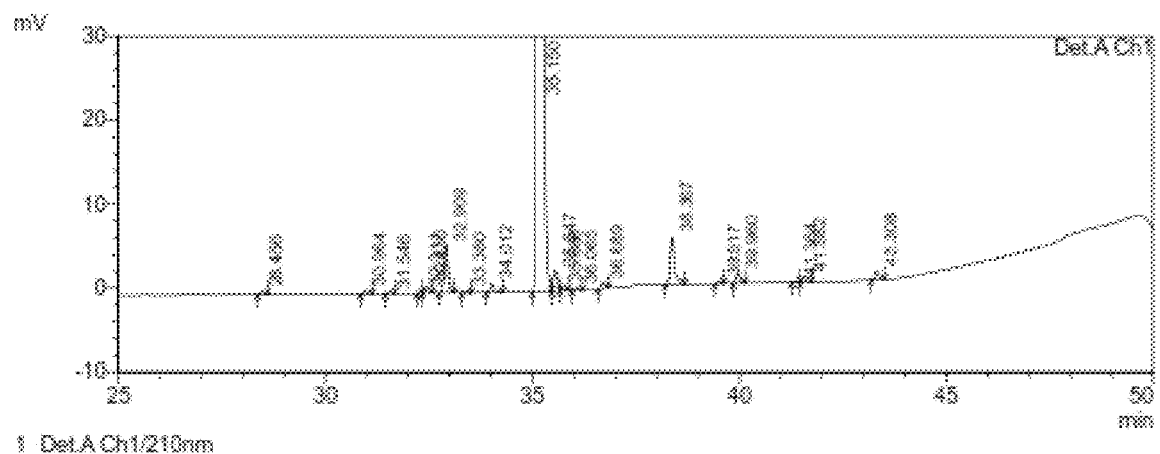
FIG. 11 is HPLC profile of Sugammadex prepared according to example 8
Figure 12:
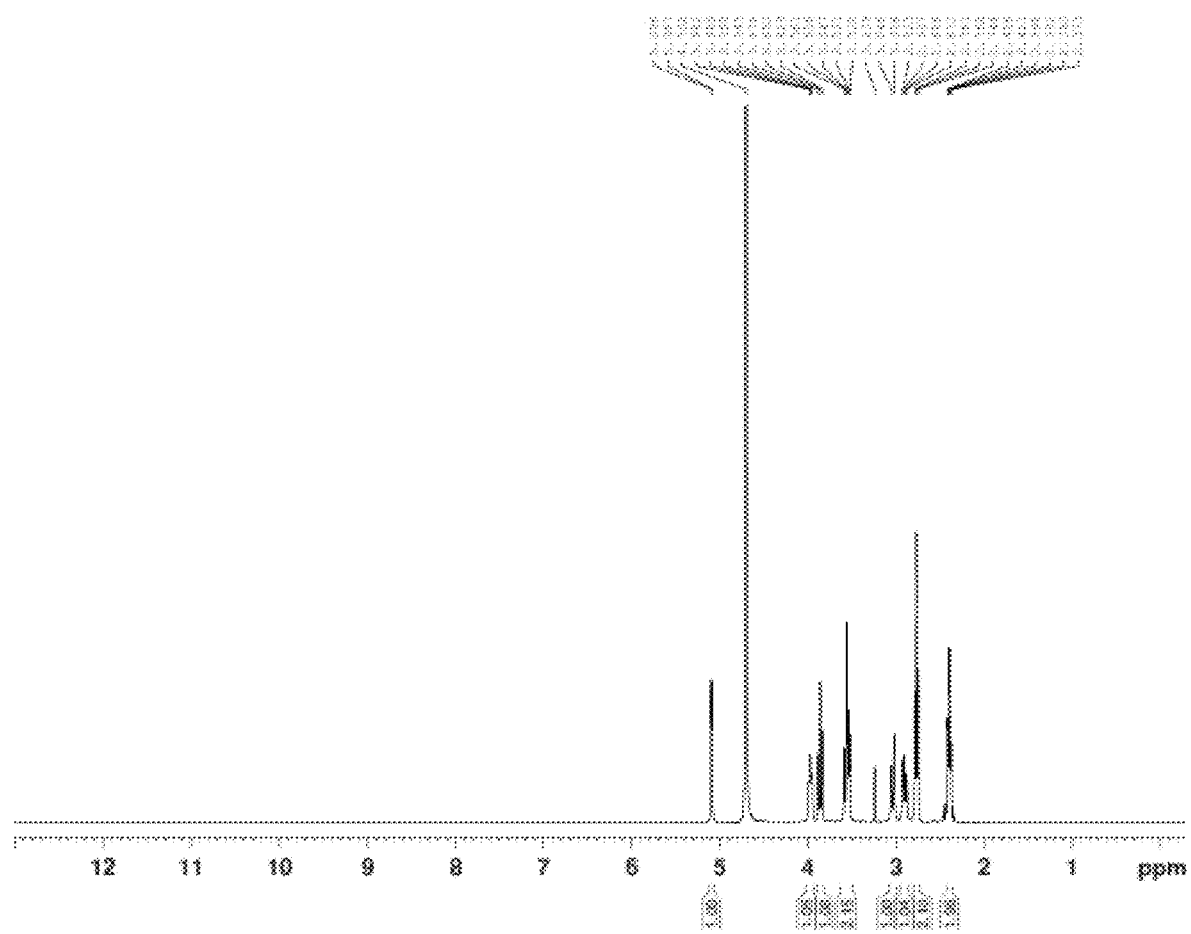
FIG. 12 is 1HNMR of Sugammadex prepared according to example 8
Figure 13:
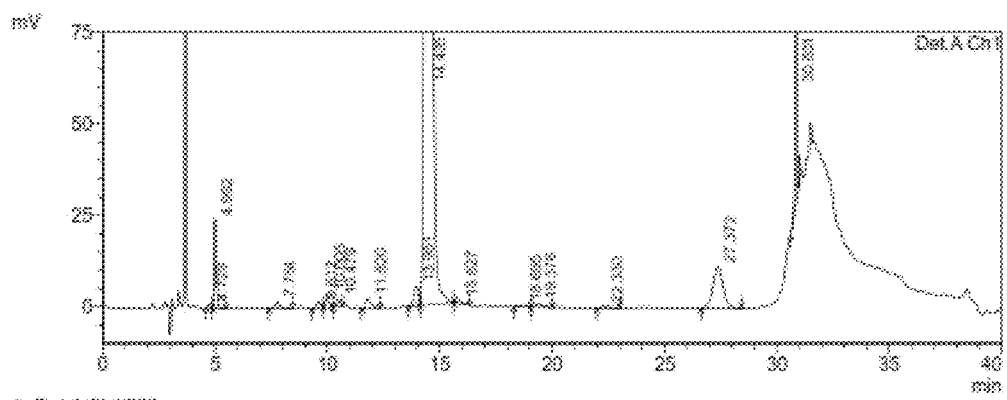
FIG. 13 is HPLC profile of Sugammadex prepared according to process of example 1 of WO2014125501.

In another embodiment, Sugammadex is purified by the preparative HPLC method. Advantageously it is found by the present inventors that Sugammadex is purified by subjecting the acid of Sugammadex sodium to preparative HPLC method. The advantage of the present process is that Sugammadex produced by preparative HPLC has purity more than 95%, preferably more than 99%. In one such embodiment purity is 99.36% as provided in FIG. 3.

Alternatively, Sugammadex sodium prepared according to the present invention is subjected to preparative HPLC method to get acid of Sugammadex having purity more than 99% which is further converted to Sugammadex sodium using sodium hydroxide to give pure Sugammadex sodium having purity more than 99%.

General conditions of HPLC method:
Chromatographic conditions of the basic preparative separation are
Reagents: (1) Acetonitrile (HPLC Grade), (2) Methanol (HPLC Grade), (3) MilliQ Water (4) Formic acid.
Diluent: Dimethyl formamide
Crude solution:
Prepare 500 mg/ml of acid of Sugammadex or Sugammadex solution by taking appropriate quantity of acid of Sugammadex and dissolve it in DMF, sonicate for 5 minutes and filter if necessary.
Mobile Phase- A
Transfer 2.0 ml of Formic acid in 1000 ml of Milli-Q water and mix well, degas by sonication and use.
Mobile Phase- B
Mixture of Acetonitrile, Methanol (70:30) respectively.
Chromatographic Conditions:
Column: Luna C18 (3), 10 µm particle size. Packed in a 50 mm id stainless steel preparative Column.
Flow rate: 35 ml/min.
Detection: UV at 210 nm
Inj. Vol.: 20 ml (Depending on concentration inject ~10.0 gms/injection)
Run time: 115 minutes
Gradient Program:

| Time in minutes | % Mobile Phase A | % Mobile Phase B |
|---|---|---|
| 0.01 | 85 | 15 |
| 10.00 | 85 | 15 |
| 20.0 | 80 | 20 |
| 80.00 | 70 | 30 |
| 100.00 | 65 | 35 |
| 101.00 | 0 | 100 |
| 110.00 | 0 | 100 |
| 110.10 | 85 | 15 |
| 115.00 | 85 | 15 |

Approximate Retention time (RT) for Sugammadex peak is 85 minutes.

Nuclear magnetic resonance spectroscopy (NMR) was performed using Avance III 400 MHz NMR spectrometer (for the 13C NMR spectra acquired at 100 MHz) and the chemical shifts were reported in δ (ppm).

The process of the present invention provides pure Sugammadex having purity at least 90%, preferably more than 95% and most preferably more than 99%.

Advantages of process of present invention:
1) Use of oxalyl halide for preparation halo cyclodextrin intermediate in present process significantly simplifies the work up procedure as no byproducts are formed and the compound obtained is having purity more than 98%. This process avoids phosphorous reagents such as PPh3, PCl5 which produces phosphorous impurities and are difficult to remove from reaction mixture. Further use of these reagents is undesirable on large scale commercial processes.
2) The inorganic base such as potassium hydroxide (KOH), sodium hydroxide (NaOH) are used in the present process for making the reaction efficient and clean. Reported use of sodium hydride and sodium methoxide require anhydrous reaction conditions. Further the anhydrous grade solvents/reagents are very expensive. The present process is economical and does not require rigorous anhydrous conditions for carrying out the reaction.
3) Greatly reduces the reaction time required for completion of reaction.
4) Simple acid base work-up procedure furnishes the desired compounds with high purity of more than 95%.

Aspects and embodiments of the present invention are illustrated by the following examples. It is to be understood, however, that the aspects and embodiments of the invention are not limited to the specific details of these examples, as other variations thereof will be known, or apparent in light of the instant disclosure, to one of ordinary skill in the art.

EXAMPLES

Example 1

Preparation of 6-perdeoxy-6-per-chloro gammacyclodextrin

In a four-neck round bottomed flask (2 L) equipped with mechanical stirrer, thermometer pocket in a tub charged anhydrous DMF (250 ml) under nitrogen atmosphere. Triphosgene (36.5 g, 0.123 mol) was added to the flask at 0-15° C. and the mixture was stirred for 1 h. Dry gamma cyclodextrin (20 g, 0.015 mol) was added to the obtained slurry with stirring for 30 min followed by addition of DMF (50 ml). The reaction mixture was heated at 65-70° C. 16 h. After the completion of reaction, the reaction mixture was cooled and diisopropyl ether (800 ml) was charged to the mixture to precipitate out the material. The solvent mixture of DMF and diisopropyl ether was decanted off from the reaction mixture to obtain gummy brown mass. The reaction mass was treated with saturated sodium bicarbonate solution (800 ml) which leads to precipitation of the solid. The precipitated solid was filtered, washed with the water (250×3 ml) and dried. This compound was used for the next step without any purification.
Yield: 95%, HPLC Purity: 99%

Example 2

Preparation of 6-perdeoxy-6-per-chloro gamma-cyclodextrin

In a 5 L four-necked flask equipped with stirrer, dropping funnel, nitrogen inlet, and thermometer with pocket, oxalyl chloride (293.8 g, 198.5 ml, 2315 mmol) was added to DMF (1200 ml) and maintained the mixture at 0-5° C. under nitrogen followed by stirring at 20-25° C. for 1 hr. A solution of gamma-cyclodextrin (100 g, 77.16 mmol) in DMF (500 ml) was added to above mixture at 5-10° C. under nitrogen. The mixture was stirred at 65-70° C. for 14-16 hr. After the completion of reaction, the reaction mixture was cooled to 20-25° C. and diluted with diisopropyl ether (1.2 L). The organic layer was decanted and the viscous residue was treated with 10% NaOH solution at 5-10° C. until PH=8. The resulting slurry was stirred for one hour at 20-25° C. The slurry was filtered under vacuum and the solid was washed with water (3×500 ml) and dried under vacuum. The crude material was suspended in methanol (750 ml), stirred for 30 min, filtered under vacuum and washed with diisopropyl ether (500 ml). The solid obtained was dried at 55-60° C. in an oven for 12-16 hr to afford the titled compound (95 g).

Yield: 85%, Purity: 98%, melting point: 226-228° C.

$^1$H NMR (400 MHz, DMSO-$d_6$): δ 6.0 (br s., 16 H), 4.99 (m, 8 H), 4.04 (d, J=10 Hz, 8 H), 3.87-3.78 (m, 16H), 3.64-3.56 (m, 8 H), 3.46-3.34 (m, 16 H) ppm.

$^{13}$C NMR (100 MHz, DMSO-$d_6$): δ 101.98, 82.93, 72.30, 72.16, 71.11, 44.92 ppm.

Mass: m/z (M+Na)$^+$ calcd for $C_{48}H_{72}C_{18}O_{32}Na$: 1463.14; found: 1463.06.

Example 3

Preparation of 6-perdeoxy-6-per-chloro gamma-cyclodextrin

In a clean, dried SOL glass reactor equipped with stirrer, dropping funnel, nitrogen inlet, and thermometer with pocket was charged anhydrous dimethylformamide (15 L, moisture content NMT 0.4%) while maintaining the temperature at 0-5° C. (using dry ice acetone bath). Oxalyl chloride (2 L, 23635 mmol, 30 eq) was added slowly over a period 4-5 hr (while maintaining the temperature below 5° C.) and stirring was continued for 1 hr at the same temperature. A solution of dry gamma-cyclodextrin (1.0 kg, 770.94 mmol) dissolved in dimethylformamide (5 L) was added slowly into the above reaction mixture. The solution was heated at 65-70° C. for 16 hr. The reaction was monitored by TLC at regular intervals. After the completion of reaction, the reaction mixture was cooled to room temperature and diisopropyl ether (10 L) was added to the reaction mixture with stirring. The gummy solid precipitate out. The upper layer solvent was decanted, the gummy brown material was cooled to 0 to 5° C. and was neutralized (pH 8.0) with slow addition of aqueous sodium hydroxide solution (20%, 5 L) with stirring. The slurry obtained was stirred for 1 hr at temperature 0 to 5° C. The precipitate was filtered, washed with the water (3×2 L) and dried under vacuum. The wet cake was suspended into methanol (10 L), stirred, filtered, washed with diisopropyl ether (2 L) and dried in oven at 60° C. for 14-16 hr to give the titled compound (980 g).

Yield: 87.9%, Purity: 98.1% as measured by HPLC.

Example 4

Preparation of Sugammadex Sodium

In a four-neck round bottomed flask (3 L) equipped with mechanical stirrer, thermometer pocket in a tub under the nitrogen atmosphere, anhydrous DMF (300 ml) and 3-Mercaptopropionic acid (18.3 g, 0.172 mol) were charged at 0-5° C. followed by addition of sodamide (20 g, 0.38 mol). The reaction mixture was stirred at the same temperature for 1 h. 6-perdeoxy-6-per-chloro gamma cyclodextrin (25 g, 0.017 mol, as obtained in example 1) was charged slowly. The reaction mixture was heated at 90-95° C. for 16 h. After completion of reaction, the reaction mixture was cooled to room temperature and methanol (300 ml) was added to it. The mixture was stirred and the precipitated material was filtered off. The precipitated material was dissolved in a mixture of methanol (50 ml) and water (50 ml) and re-precipitated with the excess addition of methanol (450 ml). The solid was filtered and dried. Yield: 76%

The dried solid was purified by the preparative HPLC method using formic acid buffer in mixture of acetonitrile and water (80:20%) followed by lyophilization to get acid of Sugammadex which is further converted to Sugammadex sodium using sodium hydroxide.

Example 5

Preparation of Sugammadex Sodium

In a four-neck round bottomed flask (5 L) equipped with mechanical stirrer, thermometer pocket in a tub under the nitrogen atmosphere, anhydrous DMF (1500 ml) and 3-mercaptopropionic acid (110 g, 1038 mmol) were charged at 0-5° C. followed by addition of sodamide (81 g, 2077 mmol). The mixture was stirred at the same temperature for 1 h. 6-perdeoxy-6-per-chloro gamma cyclodextrin (100 g, 69.25 mmol, as obtained in example 1) was charged slowly. Extra DMF (500 ml) was added to the mixture. The temperature of the mixture was raised to 80-85° C. and maintained for 16 h. After completion of reaction, the reaction mixture was cooled to room temperature and methanol (1500 ml) was added to it. The mixture was stirred and the precipitated material was filtered off. The precipitated material (wet cake) was dissolved in a mixture of methanol (800 ml) and water (800 ml). Charcoal (50 g) was added and the mixture was stirred for 30 mins at 50-55° C. The solution was filtered off through a pad of celite. Methanol (2500 ml) was added the solution and precipitated solid was filtered and dried furnishing the titled compound (105 g). Yield: 69.6%, Purity: 85.3%.

Example 6

Preparation of Sugammadex Sodium

A clean, dried 10 L four neck flask equipped with stirrer, dropping funnel, nitrogen inlet, and thermometer with pocket, was charged with a solution of sodium hydroxide (83 g, 2077 mmol) dissolved in water (100 ml) followed by addition of anhydrous DMF (2 L) maintained under inert atmosphere using nitrogen. A solution of 3-mercapto propionic acid (110 g, 1037 mmol) in DMF (1 L) was added slowly under nitrogen maintaining the temperature between 0-5° C. The mixture was stirred for another 1 hr at this temperature. A mixture of 6-deoxy-6-chloro gamma cyclodextrin (100 g, 69 mmol) in DMF (1 L) was added slowly at 5-10° C. The resulting mixture was heated to 75-80° C. for 16-20 hr. After the completion of reaction, the reaction mixture was cooled to 25-30° C. and methanol (1.5 L) was added into the reaction mixture, the resulting precipitate was stirred at 20-25° C., filtered, and dried under vacuum. The dried solid was dissolved in water (1 L), treated with activated carbon (50 g, 5%) at 50° C., stirred and filtered through celite. The filtrate was stirred at 60° C. and excess methanol (2.5 L) was added slowly to the filtrate to get the precipitate. The precipitated material was filtered under vacuum as white solid, washed with methanol (500 ml) and dried in oven to give pure Sugammadex sodium (90 g).

Yield: 90 g, Purity: 91.2%.

$^1$H NMR (400 MHz, $D_2O$): δ 5.09 (m, 8H); 3.98-3.94 (m, 8H); 3.88-3.83 (m, 8H); 3.58-3.52 (m, 16H); 3.07-3.01 (m, 8H); 2.92-2.87 (m, 8H); 2.78-2.74 (m, 16H); 2.34-2.47 (m, 16H) ppm.

$^{13}$C NMR (100 MHz, D$_2$O): δ 180.18, 100.60, 81.96, 72.14, 71.84, 70.72, 37.24, 32.83, 29.06 ppm.

Mass: m/z (M-Na$_7$+H$_6$)$^+$ calcd for C$_{72}$H$_{110}$NaO$_{48}$S$_8$: 2023.12; found: 2023.39.

Example 7

Preparation of Sugammadex Acid (Compound of Formula IV)

In a clean, dried 5 L four neck flask equipped with stirrer, dropping funnel, nitrogen inlet, and thermometer with pocket was charged dimethylformamide (1500 ml) followed by addition of potassium hydroxide (194.0 g, 3464 mmol) and the mixture maintained at 0-5° C. A solution of 3-mercapto propionic acid (186.35 g, 153.0 ml, 1756 mmol) in DMF (500 ml) was added to the reactor over a period of 30 minutes under nitrogen while maintaining the temperature between 0-5° C. The resulting mixture was stirred at this temperature for 60 minutes. A solution of 6-deoxy-6-chloro gamma cyclodextrin (100 g, 69.22 mmol) in DMF (500 ml) was added to the flask. The resulting mixture was heated at 110-120° C. for 1.5-2 hr while monitoring the progress of the reaction through HPLC. After completion of the reaction, the temperature of the reaction mixture was brought to 40-50° C. and methanol (1000 ml) was added to the mixture. The resulted precipitate was stirred at 20-25° C. for 1 hr, filtered under vacuum and washed with methanol (500 ml). The wet solid was dissolved in water (2000 ml) with vigorous stirring and the solution was acidified with concentrated hydrochloric acid to give the white solid precipitate. The precipitated solid was filtered and suspended in ethyl acetate (500 ml), stirred for 30 minutes and filtered. The solid was dried to afford the titled compound (75 g).

Yield: 55%, Purity: 95.8% as measured by HPLC.

$^1$H NMR (400 MHz, DMSO-d$_6$): δ 5.94 (br. s, 16H), 3.82-3.73 (m, 8H), 3.63-3.54 (m, 8H), 3.43-3.32 (m, 16H), 3.08-3.02 (m, 8H), 2.89-2.81 (m, 8H), 2.78-2.72 (m, 16H), 2.55-2.43 (m, 16H) ppm.

$^{13}$C NMR (100 MHz, DMSO-d$_6$): δ 173.00, 102.01, 83.94, 72.45, 72.33, 71.36, 34.53, 33.08, 27.87 ppm.

Mass: m/z (M-H$_2$+K)$^+$ calcd for C$_{72}$H$_{110}$O$_{48}$S$_8$K: 2039.24; found: 2039.26.

Example 8

Preparation of Sugammadex Sodium

In a clean, dried 3 L four neck flask equipped with stirrer, dropping funnel, nitrogen inlet, and thermometer with pocket, the compound (75 g) as obtained in example 4 was dissolved in solution of sodium hydroxide (37.5 g, 0.937 mol) in water (100 ml) and methanol (100 ml). The pH of resultant mixture was maintained between 8-10. To this mixture methanol (1.5 L) was slowly added at room temperature and the mixture was stirred for additional 30 minutes. The precipitated white solid was filtered off under vacuum and thoroughly washed with methanol (500 ml). The solid was dried at 50° C. under vacuum oven for 24 hr to afford Sugammadex sodium (79 g).

Yield: 96.9%, Purity: 95.5% measured by HPLC.

We claim:

1. A process for preparation of Sugammadex sodium comprising a) reacting gamma- cyclodextrin (II) with triphosgene or oxalyl chloride in presence of dimethylformamide to obtain perdeoxy-6-per-chloro gamma cyclodextrin (III); b) converting perdeoxy-6-per- chloro gamma cyclodextrin to Sugammadex sodium of formula (I) wherein said conversion of perdeoxy-6-per-chloro gamma cyclodextrin to Sugammadex comprises one of the following:
reacting perdeoxy-6-per-chloro gamma cyclodextrin with 3-mercapto propionic acid and sodium hydroxide to obtain Sugammadex;
OR
reacting 6-perdeoxy-6-per-chloro gamma cyclodextrin with 3-mercaptopropionic acid in presence of sodium amide to obtain Sugammadex
OR
(a) reacting 3-mercapto propionic acid and potassium hydroxide in presence of dimethylformamide to obtain a clear solution of potassium salt of 3-mercapto propionic acid;
(b) treating potassium salt of 3-mercapto propionic acid obtained in step a) with perdeoxy-6-per-halo gamma cyclodextrin to obtain a product containing potassium salt of acid of Sugammadex;
(c) treating the compound of step b) with acid to obtain a compound of formula (IV);
(d) reacting the compound of formula (IV) with sodium hydroxide to obtain Sugammadex of formula (I);
wherein the process further comprises purifying acid of Sugammadex or Sugammadex by preparative HPLC.

2. The process as claimed in claim 1 comprising subjecting acid of Sugammadex to purification.

3. A process for preparation of Sugammadex sodium comprising a) reacting gamma- cyclodextrin (II) with triphosgene or oxalyl chloride in presence of dimethylformamide to obtain perdeoxy-6-per-chloro gamma cyclodextrin (III); b) converting perdeoxy-6-per-chloro gamma cyclodextrin to Sugammadex sodium of formula (I) wherein said conversion of perdeoxy-6-per-chloro gamma cyclodextrin to Sugammadex comprising:
(a) reacting 3-mercapto propionic acid and potassium hydroxide in presence of dimethylformamide to obtain a clear solution of potassium salt of 3-mercapto propionic acid;
(b) treating potassium salt of 3-mercapto propionic acid obtained in step a) with perdeoxy- 6-per-halo gamma cyclodextrin to obtain a product containing potassium salt of acid of Sugammadex;
(c) treating the compound of step b) with acid to obtain a compound of formula (IV);
(d) reacting the compound of formula (IV) with sodium hydroxide to obtain Sugammadex of formula (I).

4. The process as claimed in claim 3, wherein the obtained Sugammadex of formula (I) has at least 95% purity.

5. A process for preparation of Sugammadex sodium comprising a) reacting gamma- cyclodextrin (II) with triphosgene or oxalyl chloride in presence of dimethylformamide to obtain perdeoxy-6-per-chloro gamma cyclodextrin (III); b) converting perdeoxy-6-per- chloro gamma cyclodextrin to Sugammadex sodium of formula (I)wherein said conversion of perdeoxy-6-per-chloro gamma cyclodextrin to Sugammadex comprising:
reacting 6-perdeoxy-6-per-chloro gamma cyclodextrin with 3-mercaptopropionic acid in presence of sodium amide to obtain Sugammadex.

6. The process as claimed in claim 3, wherein perdeoxy-6-per-chloro gamma cyclodextrin and mercapto propionic acid are used in a molar ratio of at least 1:15 and perdeoxy-6-per-chloro gamma cyclodextrin and potassium hydroxide are used in a molar ratio of at least 1:30.

7. The process as claimed in claim 6 wherein perdeoxy-6-per-chloro gamma cyclodextrin and mercapto propionic acid are used in a molar ratio of at least 1:20 and perdeoxy- 6-per-chloro gamma cyclodextrin and potassium hydroxide are used in a molar ratio of at least 1:40.

8. The process as claimed in claim 6 wherein perdeoxy-6-per-chloro gamma cyclodextrin and mercapto propionic acid are used in a molar ratio of at least 1:25 and perdeoxy-6-per-chloro gamma cyclodextrin and potassium hydroxide are used in a molar ratio of at least 1:50.

\* \* \* \* \*